(12) United States Patent
Hogwood et al.

(10) Patent No.: US 10,806,873 B2
(45) Date of Patent: Oct. 20, 2020

(54) AEROSOL-GENERATING SYSTEM COMPRISING A RESILIENT MEMBER

(71) Applicant: Philip Morris Products S.A., Neuchatel (CH)

(72) Inventors: Jonathan Hogwood, Royston (GB); Stuart Michael Ruan Jones, Royston (GB); John Antony Stephenson, Cambridge (GB); David Edington, St Albans (GB); Christopher Coulson, London (GB)

(73) Assignee: Philip Morris Products S.A., Neuchatel (CH)

(*) Notice: Subject to any disclaimer, the term of this patent is extended or adjusted under 35 U.S.C. 154(b) by 362 days.

(21) Appl. No.: 15/559,480

(22) PCT Filed: Mar. 24, 2016

(86) PCT No.: PCT/EP2016/056579
§ 371 (c)(1),
(2) Date: Sep. 19, 2017

(87) PCT Pub. No.: WO2016/156217
PCT Pub. Date: Oct. 6, 2016

(65) Prior Publication Data
US 2018/0104425 A1    Apr. 19, 2018

(30) Foreign Application Priority Data
Mar. 27, 2015   (EP) ...................................... 15161529

(51) Int. Cl.
*A61M 15/06*   (2006.01)
*A24F 47/00*   (2020.01)
(Continued)

(52) U.S. Cl.
CPC ........... *A61M 15/06* (2013.01); *A24F 47/008* (2013.01); *A61M 11/042* (2014.02);
(Continued)

(58) Field of Classification Search
CPC ................ A61M 15/06; A61M 15/009; A61M 15/0003; A61M 15/0035;
(Continued)

(56) References Cited

U.S. PATENT DOCUMENTS 9,380,810 B2 *   7/2016   Rose ........................ A24F 42/60
9,687,027 B2 *   6/2017   Poston ................... A61M 15/06
(Continued)

FOREIGN PATENT DOCUMENTS

CN         101626700 A      1/2010
CN         101951796 A      1/2011
(Continued)

OTHER PUBLICATIONS

International Search Report and Written Opinion dated Jun. 14, 2016 in PCT/EP2016/056579, filed Mar. 24, 2016.
(Continued)

*Primary Examiner* — Kendra D. Carter
*Assistant Examiner* — Thomas W Greig
(74) *Attorney, Agent, or Firm* — Oblon, McClelland, Maier & Neustadt, L.L.P.

(57) ABSTRACT

An aerosol-generating system is provided, including an aerosol-generating device including a heater element; an aerosol-generating article, including a medicament source and a volatile delivery enhancing compound source; and at least one resilient member provided in the aerosol-generating device or the aerosol-generating article and being resiliently biased against the heater element, wherein at least one of the medicament source and the volatile delivery enhancing compound source contacts the at least one resilient
(Continued)

member, and the aerosol-generating system is configured to heat the medicament source and the volatile delivery enhancing compound source of the aerosol-generating article so that the medicament source has a higher temperature than that of the volatile delivery enhancing compound source.

14 Claims, 9 Drawing Sheets

(51) Int. Cl.
  *A61M 11/04*    (2006.01)
  *A61M 15/00*    (2006.01)
  *H05B 1/02*    (2006.01)
  *H05B 3/44*    (2006.01)

(52) U.S. Cl.
  CPC ...... *A61M 11/047* (2014.02); *A61M 15/0045* (2013.01); *H05B 1/0213* (2013.01); *H05B 3/44* (2013.01); *A61M 15/0003* (2014.02); *A61M 15/0025* (2014.02); *A61M 15/0035* (2014.02); *A61M 2202/0468* (2013.01); *A61M 2205/3368* (2013.01); *A61M 2205/364* (2013.01); *A61M 2205/3646* (2013.01); *A61M 2205/3653* (2013.01); *A61M 2205/75* (2013.01); *A61M 2205/8206* (2013.01)

(58) Field of Classification Search
  CPC .... A61M 2202/3368; A61M 2202/364; A61M 11/042; A24F 47/002; A24F 47/008
  See application file for complete search history.

(56) References Cited

U.S. PATENT DOCUMENTS

| | | | |
|---|---|---|---|
| 9,974,329 B2* | 5/2018 | Buehler | A24F 47/004 |
| 9,999,247 B2* | 6/2018 | Ruscio | A24F 47/008 |
| 10,085,482 B2* | 10/2018 | Silvestrini | A24B 15/16 |
| 2007/0283972 A1 | 12/2007 | Monsees et al. | |
| 2008/0241255 A1* | 10/2008 | Rose | A61K 31/4439 |
| | | | 424/489 |
| 2008/0276947 A1 | 11/2008 | Martzel | |
| 2009/0151717 A1 | 6/2009 | Bowen et al. | |
| 2009/0260641 A1 | 10/2009 | Monsees et al. | |
| 2009/0260642 A1 | 10/2009 | Monsees et al. | |
| 2009/0293892 A1* | 12/2009 | Williams | A24F 47/008 |
| | | | 131/328 |
| 2014/0000638 A1 | 1/2014 | Sebastian et al. | |
| 2014/0261488 A1* | 9/2014 | Tucker | A24F 47/008 |
| | | | 131/328 |
| 2014/0366898 A1* | 12/2014 | Monsees | A24F 47/008 |
| | | | 131/329 |
| 2015/0150308 A1 | 6/2015 | Monsees et al. | |
| 2015/0157056 A1 | 6/2015 | Bowen et al. | |
| 2016/0022930 A1* | 1/2016 | Greim | A61M 15/06 |
| | | | 131/328 |
| 2016/0081395 A1* | 3/2016 | Thorens | A61M 11/042 |
| | | | 128/202.21 |
| 2017/0303581 A1* | 10/2017 | Schaller | A24F 47/008 |
| 2017/0347706 A1* | 12/2017 | Aoun | F22B 1/284 |
| 2018/0104425 A1 | 4/2018 | Hogwood | |

FOREIGN PATENT DOCUMENTS

| | | |
|---|---|---|
| CN | 102014995 A | 4/2011 |
| CN | 104023568 A | 9/2014 |
| CN | 104114049 A | 10/2014 |
| JP | 2014-534813 A | 12/2014 |
| WO | WO 2007/012007 A2 | 1/2007 |
| WO | WO 2008/121610 A1 | 10/2008 |
| WO | WO 2011/034723 A1 | 3/2011 |
| WO | WO 2013/040193 A2 | 3/2013 |
| WO | WO 2014/004648 A1 | 1/2014 |
| WO | WO 2014/140320 A1 | 9/2014 |
| WO | WO 2014/187770 A2 | 11/2014 |
| WO | 2015/000974 A1 | 1/2015 |
| WO | WO 2015/082652 A1 | 6/2015 |

OTHER PUBLICATIONS

Extended European Search Report dated Sep. 10, 2015 in Patent Application No. 15161529.1.
Combined Chinese Office Action and Search Report dated Dec. 3, 2019, in Patent Application No. 201680016624.X (with English translation), 11 pages.
International Search Report and Written Opinion dated Jun. 10, 2016 in PCT/EP2016/056574, filed Mar. 24, 2016.
Combined Chinese Office Action and Search Report dated Sep. 16, 2019 in Chinese Patent Application No. 201680015136.7 (with English translation), 10 pages.
U.S. Office Action dated Dec. 6, 2019 in corresponding U.S. Appl. No. 15/555,717 (11 pages).
Office Action issued in corresponding Japanese Application No. 2017-548157 (with English translation), 5 pages.
Chinese Notice of Allowance dated Jul. 14, 2020 in corresponding Chinese Patent Application No. 201680016624.X, 4 pages.

* cited by examiner

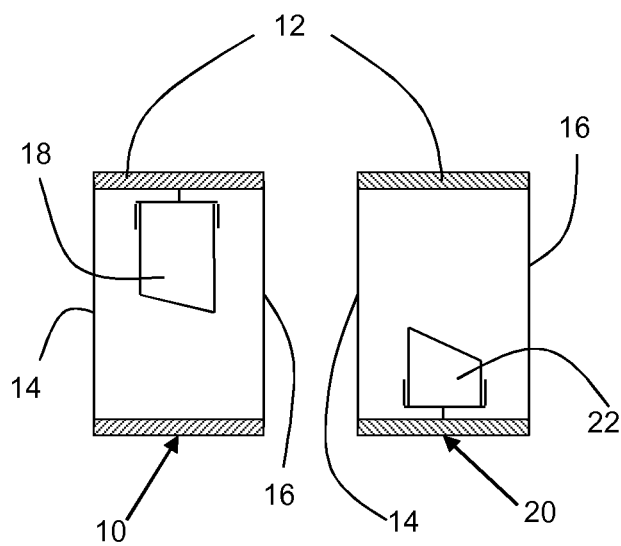
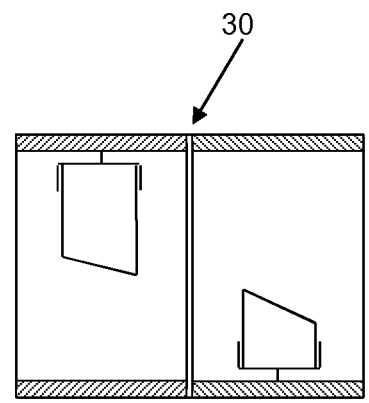
Figure 1
Figure 2
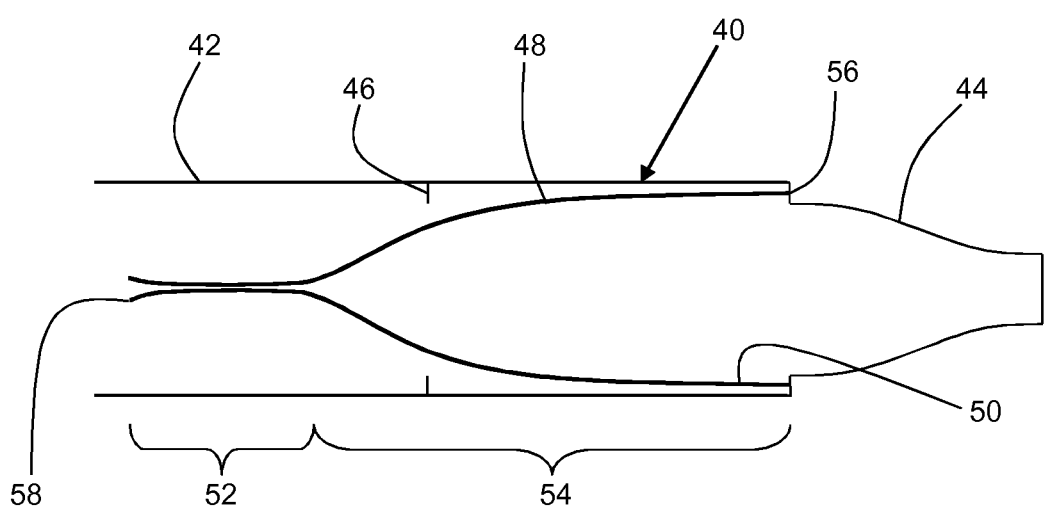
Figure 3

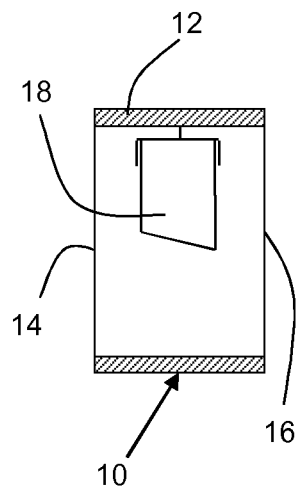
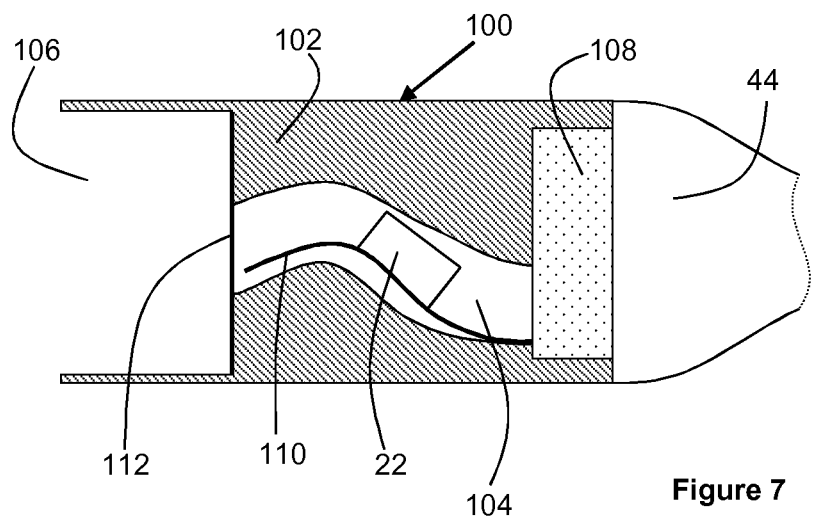
Figure 6
Figure 7
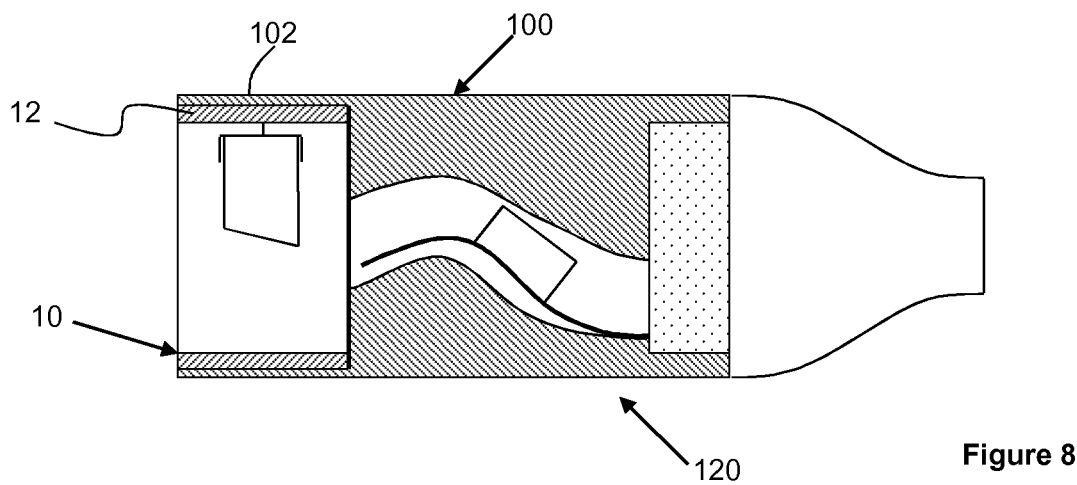
Figure 8
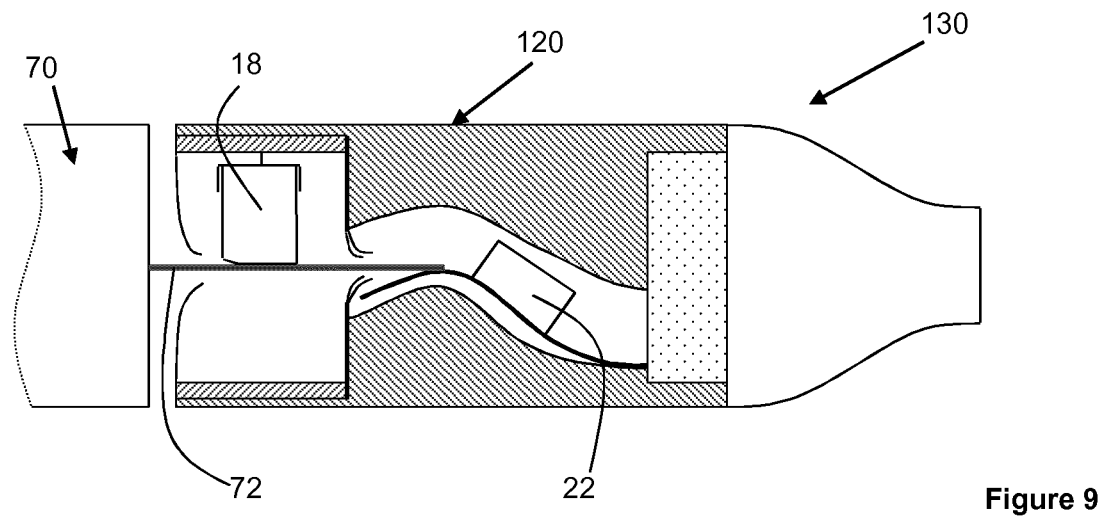
Figure 9

AEROSOL-GENERATING SYSTEM COMPRISING A RESILIENT MEMBER

The present invention relates to an aerosol-generating system for generating an aerosol comprising a medicament. The invention finds particular application as an aerosol-generating system for generating an aerosol comprising nicotine salt particles.

Some devices for delivering nicotine or other medicaments to a user comprise a volatile acid, such as pyruvic acid, or other volatile delivery enhancing compound source and a nicotine or other medicament source. The volatile delivery enhancing compound is reacted with nicotine in the gas phase to form an aerosol of nicotine salt particles that is inhaled by the user.

At room temperature pyruvic acid and nicotine are both sufficiently volatile to form respective vapours that react with one another in the gas phase to form nicotine pyruvate salt particles. However, the vapour pressure of pyruvic acid at room temperature is substantially greater than that of nicotine leading to a difference in the vapour concentration of the two reactants. Differences between the vapour concentration of the volatile delivery enhancing compound and nicotine in devices can disadvantageously lead to the delivery of unreacted delivery enhancing compound vapour to a user.

WO 2014/004648 A1 describes an electrically heated smoking article that attempts to mitigate this problem by providing first and second reservoirs containing first and second components of an aerosol precursor composition, wherein first and second wicks having different transport properties wick the first and second components of the aerosol precursor composition at different rates to a single heater, or wherein separate heaters heat the first and second components of the aerosol precursor composition to different temperatures. However, the use of multiple wicks formed from different materials or multiple heaters configured to heat the first and second components of the aerosol precursor composition to different temperatures adds complexity and cost to the manufacture of the electrically heated smoking article.

Therefore, in devices comprising a nicotine or other medicament source and a volatile delivery enhancing compound source it would be desirable to produce a maximum quantity of medicament salt particles for delivery to a user using a minimum quantity of reactants and using a relatively simple and cost effective delivery system. Consequently, it would be desirable to provide a relatively simple and cost effective aerosol-generating system in which the quantity of unreacted volatile delivery enhancing agent is minimised.

The present invention provides an aerosol-generating system comprising an aerosol-generating device comprising a heater element, and an aerosol-generating article. The aerosol-generating article comprises a medicament source and a volatile delivery enhancing compound source. The aerosol-generating system also comprises at least one resilient member provided in the aerosol-generating device or the aerosol-generating article and resiliently biased against the heater element. At least one of the medicament source and the volatile delivery enhancing compound source contacts the at least one resilient member, and the aerosol-generating system is configured to heat the medicament source and the volatile delivery enhancing compound source of the aerosol-generating article so that the medicament source has a higher temperature than the volatile delivery enhancing compound source.

As used herein, the term "aerosol-generating device" refers to a device that interacts with an aerosol-generating article to generate an aerosol that is directly inhalable into a user's lungs thorough the user's mouth.

As used herein, the term "aerosol-generating article" refers to an article comprising an aerosol-forming substrate capable of releasing volatile compounds, which can form an aerosol. The aerosol-generating article may comprise an aerosol-forming substrate capable of releasing upon heating volatile compounds, which can form an aerosol. An aerosol-generating article may be entirely consumable and mainly comprise a medicament source and a volatile delivery enhancing compound. An aerosol-generating article may comprise a reusable portion, such as a mouthpiece configured for attachment to an aerosol-generating device, and a consumable portion comprising the medicament and volatile delivery enhancing compound sources and configured for insertion into the reusable portion.

As used herein, the term "aerosol-generating system" refers to a combination of an aerosol-generating article with an aerosol-generating device.

As used herein, the term "medicament source" refers to a source of one or more volatile compounds intended for delivery to the lungs of a user. In preferred embodiments, the medicament source comprises a nicotine source.

As used herein, the term "volatile delivery enhancing compound source" refers to a source of one or more volatile compounds that react with the medicament source in the gas phase to aid delivery of the one or more compounds from the medicament source to the user.

As used herein, the term "resilient member" refers to a part of the aerosol-generating system that resists movement or deformation upon application of a force to the resilient member. Once an applied force is removed a resilient member will at least partially return to its position or shape prior to the application of the force. For example, a spring, such as a cantilever spring, can be used to form a resilient member.

By providing at least one of the medicament source and the volatile delivery enhancing compound source in contact with a resilient member that contacts the heater element, it is possible to provide an aerosol-generating system configured to differentially heat the medicament source and the volatile delivery enhancing compound source using a single heater element. An aerosol-generating system in accordance with the present invention can therefore allow precise control of the amount of volatile delivery enhancing compound vapour and medicament vapour released from the volatile delivery enhancing compound source and the medicament source respectively. This advantageously enables the vapour concentrations of the volatile delivery enhancing compound and the medicament to be controlled and balanced proportionally to yield an efficient reaction stoichiometry. This advantageously improves the efficiency of the formation of an aerosol and the consistency of the medicament delivery to a user. It also advantageously reduces the delivery of unreacted delivery enhancing compound vapour and unreacted medicament vapour to a user. Advantageously, facilitating the use of a single heater element to differentially heat the medicament source and the volatile delivery enhancing compound source can simplify and reduce of the cost of the aerosol-generating system when compared to known systems, such as that described in WO 2014/004648 A1.

The heater element is preferably an elongate heater element, such as a heater blade, for example. The elongate heater element may comprise a proximal end attached to the aerosol-generating device and a free distal end inserted into the aerosol-generating article. The distance between the proximal end of the heater element and the medicament source is less than the distance between the proximal end of the heater element and the volatile delivery enhancing compound source. By placing the medicament source closer to the proximal end of the heater element, differential heating of the medicament source and the volatile delivery enhancing compound source can be achieved using a single heater element.

The at least one resilient member may comprises first and second resilient members each resiliently biased against the heater element so that the heater element is positioned between the first and second resilient members. In such embodiments, the heater element is effectively grasped between the first and second resilient members, which advantageously ensures a good contact between the heater element and the resilient members, and therefore optimises conduction of heat from the heater element to the at least one of the medicament and volatile delivery enhancing compound source that contacts one or both of the resilient members.

The first and second resilient members may be formed from two separate components, each forming one of the resilient members. Alternatively, a single component can be shaped to form both of the first and second resilient members. For example, a resilient material can be bent or otherwise shaped so that two ends of the resilient material come into contact or close proximity with each other and therefore form the first and second resilient members between which the heater element is grasped.

Each of the first and second resilient members may comprise a first portion resiliently biased against the heater element and a second portion spaced apart from the heater element, and wherein the volatile delivery enhancing compound source contacts the second portion of one of the first and second resilient members. Providing the volatile delivery enhancing compound source on one of the resilient members on a portion that is not in direct contact with the heater element facilitates differential heating of the medicament and volatile delivery enhancing compound source. In particular, by eliminating direct contact between the heater element and the portion of the resilient member on which the volatile delivery enhancing compound source is provided, the volatile delivery enhancing compound source can be heated to a lower temperature than the medicament source.

To prevent contact between the heater element and the second portion of the first and second resilient members the second portion of each resilient member may be positioned downstream of the heater element. Additionally, or alternatively, each of the first and second resilient members may be shaped so that the second portions of the resilient members are spaced apart from the heater element in a transverse direction. For example, the first and second resilient members may be shaped so that together they form a "wishbone" shape, wherein the first portions of the resilient members come together to form a V-shaped tip to the wishbone shape and the second portions extend away from each other in the transverse direction and extend downstream from the first portions.

As used herein, the terms "upstream" and "downstream" are used to describe the relative positions of components, or portions of components, of aerosol-generating systems according to the invention. The aerosol-generating system comprises a downstream end through which in use an aerosol exits the aerosol-generating article. The downstream end may also be referred to as the mouth end. In use, a user draws on the downstream or mouth end of the aerosol-generating system in order to inhale an aerosol generated by the aerosol-generating article. The aerosol-generating article comprises an upstream end opposed to the downstream or mouth end.

As used herein, the term "longitudinal direction" is used to refer to the direction extending between the upstream and downstream end of the aerosol-generating system. The term "transverse direction" is used herein to refer to a direction perpendicular to the longitudinal direction.

In those embodiments in which the volatile delivery enhancing compound contacts a second portion of the first or second resilient member, wherein the second portion is spaced apart from the heater element, the medicament source may contact the first portion of one of the first and second resilient members. That is, the medicament source may contact the first or second resilient members on a portion that is in direct contact with the heater element. Alternatively, the medicament source may be arranged so that it contacts the heater element. In this case, a thin barrier, such as a thin sheet of metal foil, may be provided on the surface of the medicament source in contact with the heater element to prevent transfer of the medicament to the heater element. Both of these embodiments facilitate differential heating of the medicament source and the volatile delivery enhancing compound source by providing optimum heat transfer from the heater element to the medicament source, therefore heating the medicament source to a higher temperature than the volatile delivery enhancing compound source.

In any of the embodiments comprising one or more resilient members, each of the resilient members is preferably formed from a material that is both thermally conductive and can withstand the operating temperature of the heater element. Preferably, each of the resilient members is formed from a metal or a metal alloy.

In any of the embodiments described above, the aerosol-generating article may comprise a housing containing the medicament source, the volatile delivery enhancing compound source and the at least one resilient member. The medicament source contacts the at least one resilient member, and the volatile delivery enhancing compound source and the at least resilient member contact the housing so that heat is conducted from the heater element to the volatile delivery enhancing compound through the at least one resilient member and the housing. Providing the medicament source in direct contact with the at least one resilient member, and the volatile delivery enhancing compound source in indirect contact with the at least one resilient member via the housing, facilitates differential heating of the medicament source and the volatile delivery enhancing compound source.

To facilitate the conduction of heat from the heater element to the volatile delivery enhancing compound source, the housing preferably comprises a heat conductive element forming at least part of an inner surface of the housing, wherein the at least one resilient member and the volatile delivery enhancing compound source contact the heat conductive element.

The medicament source may contact the heater element and the volatile delivery enhancing compound source contacts the at least one resilient member. This arrangement assists in providing the differential heating of the two sources by allowing heat to be conducted directly from the heater element to the medicament source, therefore heating the medicament source to a higher temperature than the volatile delivery enhancing compound source. A thin barrier, such as a thin sheet of metal foil, may be provided on the surface of the medicament source in contact with the heater element to prevent transfer of the medicament to the heater element.

In any of the embodiments in which the volatile delivery enhancing compound source contacts the at least one resilient member, the at least one resilient member may comprise a bimetallic strip comprising a first end in contact with the heater element and a second end in contact with the volatile delivery enhancing compound source. The bimetallic strip is configured so that heating the first end of the bimetallic strip above a predetermined temperature results in displacement of the first end of the bimetallic strip away from the heater element. The bimetallic strip effectively provides thermostatic control of the temperature to which the volatile delivery enhancing compound source is heated. Therefore, the heater element can be configured to reach a sufficiently high temperature to heat the medicament source to a higher temperature than the volatile delivery enhancing compound source without overheating the volatile delivery enhancing compound source. Using a bimetallic strip to conduct heat from the heater element to the volatile delivery enhancing compound source therefore facilitates the use of a single heater element to provide differential heating of the two sources.

The first end of the bimetallic strip may be in direct contact with the heater element. Alternatively, the first end of the bimetallic strip may contact the heater element via one or more intervening thermally conductive components. In these latter embodiments, the bimetallic strip is configured so that when the first end of the bimetallic strip is heated above the predetermined temperature the first end of the bimetallic strip is displaced away from the one or more intervening thermally conductive components, or the bimetallic strip and the one or more intervening thermally conductive components are both displaced away from the heater element if the one or more thermally conductive components are secured to the first end of the bimetallic strip.

Similarly, the second end of the bimetallic strip may be in direct contact with the volatile delivery enhancing compound source. Alternatively, the second end of the bimetallic strip may contact the volatile delivery enhancing compound source via one or more intervening thermally conductive components.

The bimetallic strip may comprise a simple linear bimetallic strip forming a cantilever having a first moveable end in contact with the heater element and a second fixed end in contact with the volatile delivery enhancing compound source. Alternatively, the bimetallic strip may be formed into a more complex shape, such as a bimetallic spiral. The particular shape of the bimetallic strip may be selected depending on the particular thermostatic control required to provide the differential heating of the volatile delivery enhancing compound source. In particular, the choice of metals in combination with the shape of the bimetallic strip can provide a desired speed of response, size of movement and thermal power transfer of the bimetallic strip.

The bimetallic strip may be formed from two layers of metal or metal alloy having different coefficients of thermal expansion. The two layers may be joined together by any suitable conventional process, such as cladding. Suitable metals for forming the first and second layers include aluminium, aluminium alloys, beryllium alloys, bismuth, brass, bronze, cadmium, cobalt alloys, copper, copper-nickel alloys, gold, iron, lead, magnesium, magnesium alloys, monel, nickel, nickel alloys, nickel aluminides, niobium, niobium alloys, palladium, platinum, rhenium, silver, silver alloys, steel, tantalum, tantalum alloys, tin, tin alloys, titanium, titanium aluminides, uranium, vanadium alloys, zinc, zinc alloys, and zirconium.

The at least one resilient member may comprise a single resilient member, wherein the medicament source and the volatile delivery enhancing compound source contact the single resilient member. In such embodiments, the heater element may contact a portion of the single resilient member upstream of the medicament source or adjacent the medicament source, and the volatile delivery enhancing compound source contacts the single resilient member downstream of the medicament source. Alternatively, the medicament source may be in direct contact with the heater element and the heater element contacts a portion of the single resilient member upstream of the volatile delivery enhancing compound source. In this case, a thin barrier, such as a thin sheet of metal foil, may be provided on the surface of the medicament source in contact with the heater element to prevent transfer of the medicament to the heater element.

In any of the embodiments described above, the aerosol-generating device and the aerosol-generating article may be configured to heat the medicament source to a first temperature and to heat the volatile delivery enhancing compound source to a second temperature, wherein the first temperature is at least about 50 degrees Celsius higher than the second temperature, preferably at least about 70 degrees Celsius higher than the second temperature, most preferably at least about 80 degrees Celsius higher than the second temperature. Additionally, or alternatively, the first temperature is preferably no more than about 100 degrees Celsius higher than the second temperature. Preferably, the temperature difference between the first and second temperatures is between about 50 and about 100 degrees Celsius, more preferably between about 60 and about 100 degrees Celsius, most preferably between about 80 and about 100 degrees Celsius.

In any of the embodiments described above, the aerosol-generating device and the aerosol-generating article may be configured to heat the volatile delivery enhancing compound source to a temperature of at least about 30 degrees Celsius. Additionally, or alternatively, the aerosol-generating device and the aerosol-generating article may be configured to heat the volatile delivery enhancing compound source to a temperature of less than about 100 degrees Celsius, preferably less than about 70 degrees Celsius. Preferably, the aerosol-generating device and the aerosol-generating article are configured to heat the volatile delivery enhancing compound source to a temperature of between about 30 and about 100 degrees Celsius, more preferably between about 30 and about 70 degrees Celsius.

In any of the embodiments described above, the aerosol-generating device and the aerosol-generating article may be configured to heat the medicament source to a temperature of at least about 50 degrees Celsius. Additionally, or alternatively, the aerosol-generating device and the aerosol-generating article may be configured to heat the medicament source to a temperature of less than about 150 degrees Celsius, preferably less than about 100 degrees Celsius. Preferably, the aerosol-generating device and the aerosol-generating article are configured to heat the medicament source to a temperature of between about 50 and about 150 degrees Celsius, more preferably between about 50 and about 100 degrees Celsius.

The medicament source of the aerosol-generating article may be sealed by one or more frangible barriers. Alternatively or in addition, the volatile delivery enhancing compound source of the aerosol-generating article may be sealed by one or more frangible barriers. Preferably, both sources are sealed by one or more frangible barriers.

The one or more frangible barriers may be formed from any suitable material. For example, the one or more frangible barriers may be formed from a metal foil or film.

In such embodiments, at least one of the aerosol-generating device and the aerosol-generating article preferably further comprises a rupturing member positioned for breaking the one or more frangible barriers sealing one or both of the medicament and volatile delivery enhancing compound sources of the aerosol-generating article.

The medicament source and the volatile delivery enhancing compound source are preferably arranged in series within the aerosol-generating article.

As used herein, by "series" it is meant that the medicament source and the volatile delivery enhancing compound source are arranged within the aerosol-generating article so that in use an air stream drawn through the aerosol-generating article passes through one of the medicament source and the volatile delivery enhancing compound source and then passes through the other of the medicament source and the volatile delivery enhancing compound source.

Preferably, the medicament source is upstream of the volatile delivery enhancing compound source so that in use medicament vapour is released from the medicament source into the air stream drawn through the aerosol-generating article and volatile delivery enhancing compound vapour is released from the volatile delivery enhancing compound source into the medicament-containing air stream drawn through the aerosol-generating article. The medicament vapour reacts with the volatile delivery enhancing compound vapour in the gas phase to form an aerosol, which is delivered to a user.

The medicament source and the volatile delivery enhancing compound source may be arranged in parallel within the aerosol-generating article.

The volatile delivery enhancing compound preferably has a vapour pressure of at least about 20 Pa, more preferably at least about 50 Pa, more preferably at least about 75 Pa, most preferably at least 100 Pa. Unless otherwise stated, all vapour pressures referred to herein are vapour pressures at 25° C. measured in accordance with ASTM E1194-07.

Preferably, the volatile delivery enhancing compound has a vapour pressure of less than or equal to about 400 Pa, more preferably less than or equal to about 300 Pa, even more preferably less than or equal to about 275 Pa, most preferably less than or equal to about 250 Pa at 25° C.

The volatile delivery enhancing compound may have a vapour pressure of between about 20 Pa and about 400 Pa, more preferably between about 20 Pa and about 300 Pa, even more preferably between about 20 Pa and about 275 Pa, most preferably between about 20 Pa and about 250 Pa at 25° C.

The volatile delivery enhancing compound may have a vapour pressure of between about 50 Pa and about 400 Pa, more preferably between about 50 Pa and about 300 Pa, even more preferably between about 50 Pa and about 275 Pa, most preferably between about 50 Pa and about 250 Pa at 25° C.

The volatile delivery enhancing compound may have a vapour pressure of between about 75 Pa and about 400 Pa, more preferably between about 75 Pa and about 300 Pa, even more preferably between about 75 Pa and about 275 Pa, most preferably between about 75 Pa and about 250 Pa at 25° C.

The volatile delivery enhancing compound may have a vapour pressure of between about 100 Pa and about 400 Pa, more preferably between about 100 Pa and about 300 Pa, even more preferably between about 100 Pa and about 275 Pa, most preferably between about 100 Pa and about 250 Pa at 25° C.

The volatile delivery enhancing compound may comprise a single compound. The volatile delivery enhancing compound may comprise two or more different compounds.

Where the volatile delivery enhancing compound comprises two or more different compounds, the two or more different compounds in combination have a vapour pressure of at least about 20 Pa at 25° C.

Preferably, the volatile delivery enhancing compound is a volatile liquid.

The volatile delivery enhancing compound may comprise a mixture of two or more different liquid compounds.

The volatile delivery enhancing compound may comprise an aqueous solution of one or more compounds. The volatile delivery enhancing compound may comprise a non-aqueous solution of one or more compounds.

The volatile delivery enhancing compound may comprise two or more different volatile compounds. The volatile delivery enhancing compound may comprise a mixture of two or more different volatile liquid compounds.

The volatile delivery enhancing compound may comprise one or more non-volatile compounds and one or more volatile compounds. The volatile delivery enhancing compound may comprise a solution of one or more non-volatile compounds in a volatile solvent or a mixture of one or more non-volatile liquid compounds and one or more volatile liquid compounds.

Preferably, the volatile delivery enhancing compound comprises an acid. The volatile delivery enhancing compound may comprise an organic acid or an inorganic acid. Preferably, the volatile delivery enhancing compound comprises an organic acid, more preferably a carboxylic acid, most preferably an alpha-keto or 2-oxo acid. The volatile delivery enhancing compound may comprise lactic acid. Other suitable acids includes aspartic acid, glutamic acid, salicylic acid, tartaric acid, gallic acid, levulinic acid, acetic acid, malic acid, citric acid, oxalic acid, sulphuric acid, palmitic acid, and alginic acid.

Preferably, the volatile delivery enhancing compound comprises an acid selected from the group consisting of 3-methyl-2-oxopentanoic acid, pyruvic acid, 2-oxopentanoic acid, 4-methyl-2-oxopentanoic acid, 3-methyl-2-oxobutanoic acid, 2-oxooctanoic acid and combinations thereof. Preferably, the volatile delivery enhancing compound comprises pyruvic acid.

Preferably, the volatile delivery enhancing compound source comprises a sorption element and a volatile delivery enhancing compound sorbed on the sorption element. The volatile delivery enhancing compound may be sorbed onto the sorption element during manufacture and the sorption element may be sealed. The volatile delivery enhancing compound may be stored separately from the sorption element, for example in a blister on or adjacent the sorption element. In such embodiments, the volatile delivery enhancing compound source is formed when the volatile delivery enhancing compound is released and sorbed onto the sorption element.

As used herein, by "sorbed" it is meant that the volatile delivery enhancing compound is adsorbed on the surface of the sorption element, or absorbed in the sorption element, or both adsorbed on and absorbed in the sorption element. Preferably, the volatile delivery enhancing compound is adsorbed on the sorption element.

The sorption element may be formed from any suitable material or combination of materials. For example, the sorption element may comprise one or more of glass, stainless steel, aluminium, polyethylene (PE), polypropylene, polyethylene terephthalate (PET), polybutylene terephthalate (PBT), polytetrafluoroethylene (PTFE), expanded polytetrafluoroethylene (ePTFE), and BAREX®.

In a preferred embodiment, the sorption element is a porous sorption element.

The sorption element may be a porous sorption element comprising one or more materials selected from the group consisting of porous plastic materials, porous polymer fibres and porous glass fibres.

The sorption element is preferably chemically inert with respect to the volatile delivery enhancing compound.

The sorption element may have any suitable size and shape.

The size, shape and composition of the sorption element may be chosen to allow a desired amount of volatile delivery enhancing compound to be sorbed on the sorption element.

Preferably, between about 20 μl and about 200 μl, more preferably between about 40 μl and about 150 μl, most preferably between about 50 μl and about 100 μl of the volatile delivery enhancing compound is sorbed on the sorption element.

The sorption element advantageously acts as a reservoir for the volatile delivery enhancing compound.

Preferably, the medicament has a melting point below about 150 degrees Celsius.

Alternatively or in addition, preferably the medicament has a boiling point below about 300 degrees Celsius.

In certain preferred embodiments, the medicament comprises one or more aliphatic or aromatic, saturated or unsaturated nitrogenous bases (nitrogen containing alkaline compounds) in which a nitrogen atom is present in a heterocyclic ring or in an acyclic chain (substitution).

The medicament may comprise one or more compounds selected from the group consisting of: nicotine; 7-Hydroxymitragynine; Arecoline; Atropine; Bupropion; Cathine (D-norpseudoephedrine); Chlorpheneramine; Dibucaine; Dimemorphan, Dimethyltryptamine, Diphenhydramine, Ephedrine, Hordenine, Hyoscyamine, Isoarecoline, Levorphanol, Lobeline, Mesembrine, Mitragynine, Muscatine, Procaine, Pseudo ephedrine, Pyrilamine, Raclopride, Ritodrine, Scopolamine, Sparteine (Lupinidine) and Ticlopidine; tobacco smoke constituents, such as 1,2,3,4 Tetrahydroisoquinolines, Anabasine, Anatabine, Cotinine, Myosmine, Nicotrine, Norcotinine, and Nornicotine; anti-asthmatic drugs, such as Orciprenaline, Propranolol and Terbutaline; anti-angina drugs, such as Nicorandil, Oxprenolol and Verapamil; antiarrhythmic drugs, such as Lidocaine; nicotinic agonists, such as Epibatidine, 5-(2R)-azetidinylmethoxy)-2-chloropyridine (ABT-594), (S)-3-methyl-5-(l-methyl-2-pyrrolidinyl)isoxazole (ABT 418) and (±)-2-(3-Pyridinyl)-l-azabicyclo[2.2.2]octane (RJR-2429); nicotinic antagonists, such as Methyllycacotinine and Mecamylamine; acetyl cholinesterase inhibitors, such as Galantamine, Pyridostigmine, Physostigmine and Tacrine; and MAO-inhibitors, such as Methoxy-N,N-dimethyltryptamine, 5-methoxy-α-methyltryptamine, Alpha-methyltryptamine, Iproclozide, Iproniazide, Isocarboxazide, Linezolid, Meclobemide, N,N-Dimethyltryptamine, Phenelzine, Phenyl ethylamine, Toloxatone, Tranylcypromine and Tryptamine.

Preferably, the medicament source comprises a nicotine source. The nicotine source may comprise one or more of nicotine, nicotine base, a nicotine salt, such as nicotine-HCl, nicotine-bitartrate, or nicotine-tartrate, or a nicotine derivative.

The nicotine source may comprise natural nicotine or synthetic nicotine.

The nicotine source may comprise pure nicotine, a solution of nicotine in an aqueous or non-aqueous solvent or a liquid tobacco extract.

The nicotine source may further comprise an electrolyte forming compound. The electrolyte forming compound may be selected from the group consisting of alkali metal hydroxides, alkali metal oxides, alkali metal salts, alkaline earth metal oxides, alkaline earth metal hydroxides and combinations thereof.

The nicotine source may comprise an electrolyte forming compound selected from the group consisting of potassium hydroxide, sodium hydroxide, lithium oxide, barium oxide, potassium chloride, sodium chloride, sodium carbonate, sodium citrate, ammonium sulfate and combinations thereof.

The nicotine source may comprise an aqueous solution of nicotine, nicotine base, a nicotine salt or a nicotine derivative and an electrolyte forming compound.

The nicotine source may further comprise other components including, but not limited to, natural flavours, artificial flavours and antioxidants.

The medicament source may comprise a sorption element as described above and a medicament sorbed on the sorption element. The medicament may be sorbed onto the sorption element during manufacture and the sorption element may be sealed. The medicament may be stored separately from the sorption element, for example in a blister on or adjacent the sorption element. In such embodiments, the medicament source is formed when the medicament is released and sorbed onto the sorption element.

The aerosol-generating device is configured to heat the medicament source and the volatile delivery enhancing compound source of the aerosol-generating article so that the medicament source of the aerosol-generating article has a higher temperature than the volatile delivery enhancing compound source of the aerosol-generating article. The aerosol-generating device may be configured to substantially simultaneously heat the medicament source and the volatile delivery enhancing compound source of the aerosol-generating article.

The aerosol-generating device may further comprise a controller configured to control a supply of power to the heater element.

The aerosol-generating device may further comprise a power supply for supplying power to the heater element and a controller configured to control a supply of power from the power supply to the heater element. The controller of the aerosol-generating device may be configured to control a supply of power from an external power supply to the heater element.

The heater element may be an electric heater element powered by an electric power supply. Where the heater element is an electric heater element, the aerosol-generating device may further comprise an electric power supply and a controller comprising electronic circuitry configured to control the supply of electric power from the electric power supply to the electric heater element.

The power supply may be a DC voltage source. Preferably, the power supply is a battery. The power supply may be a Nickel-metal hydride battery, a Nickel cadmium battery, or a Lithium based battery, for example a Lithium-Cobalt, a Lithium-Iron-Phosphate or a Lithium-Polymer battery. The power supply may be another form of charge storage device such as a capacitor. The power supply may require recharging and may have a capacity that allows for the storage of enough energy for use of the aerosol-generating device with one or more aerosol-generating articles.

The heater element may be a non-electric heater, such as a chemical heating means.

The heater element of the aerosol-generating device preferably comprises a single heater element to simplify the construction of the aerosol-generating device. Differential heating of the medicament source and the volatile delivery enhancing compound source may be achieved by contacting at least one of the sources with the resilient member, which in turn is biased against the heater element.

The heater element may have any suitable shape. Preferably, the heater element is an elongate heater element. In a particularly preferred embodiment, the elongate heater element has a width that is greater than the thickness of the heater element so that the heater element forms a heater blade.

Preferably, the heater element is heated electrically. However, other heating schemes may be used to heat the heater element. The heater element may be heated by conduction from another heat source. The heater element may comprise an infra-red heater element, a photonic source, or an inductive heater element.

The heater element may comprise a heat sink, or heat reservoir comprising a material capable of absorbing and storing heat and subsequently releasing the heat over time to the aerosol-forming article. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, a metal salt, a mixture of eutectic salts or an alloy.

Preferably the heater element comprises an electrically resistive material. The heater element may comprise a non-elastic material, for example a ceramic sintered material, such as alumina ($Al_2O_3$) and silicon nitride ($Si_3N_4$), or printed circuit board or silicon rubber. The heater element may comprise an elastic, metallic material, for example an iron alloy or a nickel-chromium alloy.

Other suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, nickel-, cobalt-, chromium-, aluminium-titanium-zirconium-, hafnium-, niobium-, molybdenum-, tantalum-, tungsten-, tin-, gallium- and manganese-alloys, and super-alloys based on nickel, iron, cobalt, stainless steel, Timetal® and iron-manganese-aluminium based alloys. Timetal® is a registered trade mark of Titanium Metals Corporation, 1999 Broadway Suite 4300, Denver, Colo. In composite materials, the electrically resistive material may optionally be embedded in, encapsulated or coated with an insulating material or vice-versa, depending on the kinetics of energy transfer and the external physico-chemical properties required.

The aerosol-generating device may comprise one or more temperature sensors configured to sense the temperature of at least one of the heater element, the medicament source and the volatile delivery enhancing compound source. The controller may be configured to control a supply of power to the heater element based on the sensed temperature.

The heater element may be formed using a metal having a defined relationship between temperature and resistivity. The metal may be formed as a track between two layers of suitable insulating materials. A heater element formed in this manner may be used both as a heater and a temperature sensor.

The invention will now be further described, by way of example only, with reference to the accompanying drawings in which:

FIGS. 1 and 2 show consumable portions of an aerosol-generating article in accordance with a first embodiment of the present invention;

FIG. 3 shows a reusable portion of an aerosol-generating article in accordance with the first embodiment of the present invention;

FIG. 6 shows a first consumable portion of an aerosol-generating article in accordance with a second embodiment of the present invention;

FIG. 7 shows a second consumable portion of an aerosol-generating article in accordance with the second embodiment of the present invention;

FIG. 8 shows the first and second consumable portions of FIGS. 6 and 7 combined to form an aerosol-generating article in accordance with the second embodiment of the present invention;

FIG. 9 shows an aerosol-generating device combined with the aerosol-generating article of FIG. 8 to form an aerosol-generating system in accordance with the second embodiment of the present invention;

Figure 25:
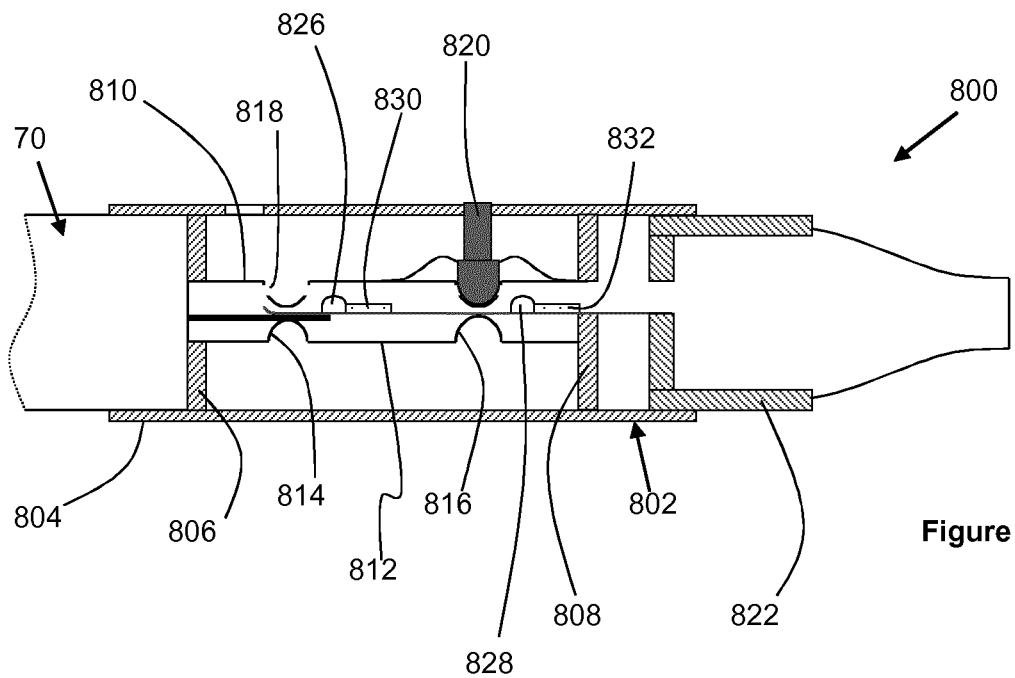
Figure 26:
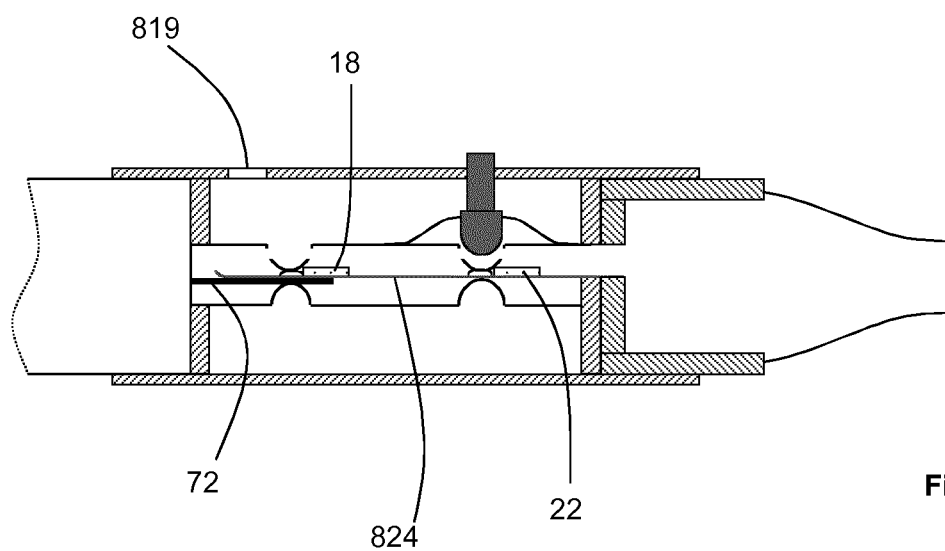

FIG. 25 shows an aerosol-generating system in accordance with a ninth embodiment of the present invention, before activation of the aerosol-generating article and with an airflow passage through the aerosol-generating article in a closed state; and FIG. 26 shows the aerosol-generating system of FIG. 25 after activation of the aerosol-generating article and with the airflow passage through the aerosol-generating article in an open state.

Like reference numerals will be used to designate like parts in the following description of the drawings.

FIG. 1 shows first and second consumable portions of an aerosol-generating article according to a first embodiment of the present invention. First consumable portion 10 comprises a tubular segment 12 sealed at both ends by frangible barriers 14 and 16 formed from a metal foil. A medicament source 18 is mounted on an inner surface of the tubular segment 12 and comprises a medicament, such as nicotine, sorbed on a porous sorption element.

Similarly, the second consumable portion 20 comprises a tubular segment 12 sealed at both ends by frangible barriers 14 and 16. A volatile delivery enhancing compound source 22 is mounted on an inner surface of the tubular segment 12 and comprises a volatile delivery enhancing compound, such as pyruvic acid, sorbed on a porous sorption element.

As shown in FIG. 2, the first and second consumable portions 10 and 20 are secured together to form a consumable 30 that is inserted into a reusable portion of the aerosol-generating article. The first and second consumable portions can be secured together using any suitable means, such as an interference fit between the ends of the tubular segments 12.

FIG. 3 shows the reusable portion 40 of the aerosol-generating article, the reusable portion comprising a tubular outer housing 42 and a mouthpiece 44 at the downstream end of the outer housing 42. The mouthpiece 44 may be formed integrally with the outer housing 42, or the mouthpiece 44 may be formed separately and secured to the upstream end of the outer housing 42, for example using an interference fit. The outer housing 42 and the mouthpiece 44 are formed from a rigid, thermally insulating material, such as a plastic.

The upstream end of the outer housing 42 is open to receive the consumable 30, and stops 46 are provided on an inner surface of the outer housing 42 to limit the insertion of the consumable 30 into the reusable portion 40.

Provided in the outer housing 42 are a pair of opposed resilient members 48 and 50. The resilient member 48 and 50 are shaped so that together they form a "wishbone" shape comprising upstream portions 52 positioned adjacent each other and downstream portions 54 spaced apart from each other. Each resilient member is secured at its downstream end 56 to the outer housing 42. The upstream ends 58 of the resilient members 48 and 50 are curved away from each other to provide a "mouth" to facilitate insertion of a heater element between the upstream portions 52 of the resilient members. The resilient members 48 and 50 are formed from a thermally conductive resilient material, such as a metal, capable of withstanding the operating temperature of the heater element when inserted between the upstream portions 52 of the resilient members.

Figure 4:
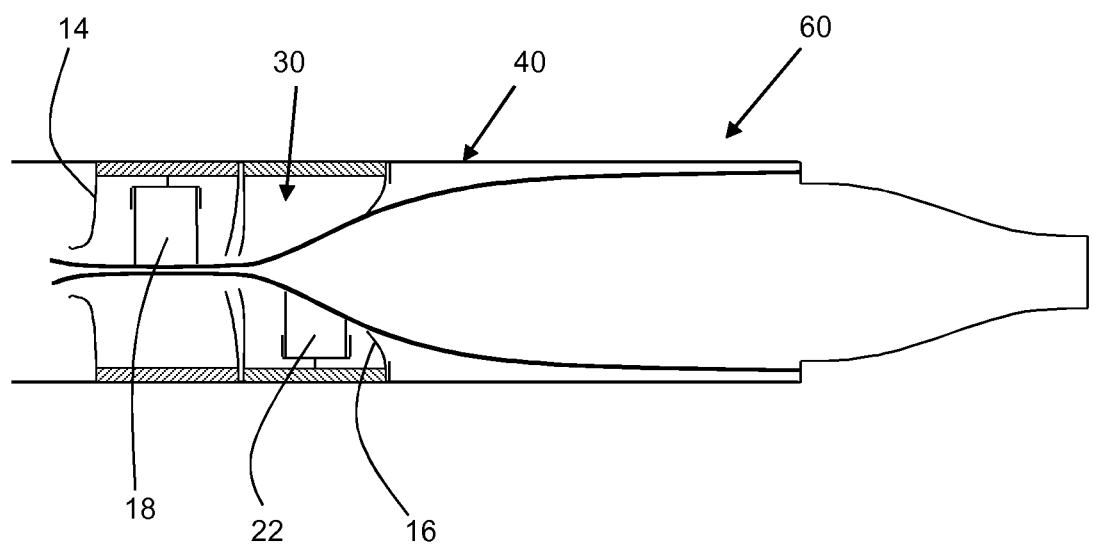
FIG. 4 shows the consumable portions of FIGS. 1 and 2 combined with the reusable portion of FIG. 3 to form an aerosol-generating article in accordance with the first embodiment of the present invention.

FIG. 4 shows the consumable 30 inserted into the reusable portion 40 to form the aerosol-generating article 60 according to the first embodiment of the invention. Upon inserting the consumable 30 into the upstream end of the outer housing 42, the resilient members 48 and 50 puncture the frangible barriers 14 and 16 sealing the first and second consumable portions 10 and 20, therefore allowing air to flow into the upstream end of the outer housing 42, through the consumable 30, around the resilient members 48 and 50 and out of the aerosol-generating article 60 through the mouthpiece 44.

The consumable 30 is inserted into the upstream end of the outer housing 42 until the downstream end of the consumable 30 abuts the stops 46. At this point, the consumable 30 is fully inserted into the reusable portion 40 so that the medicament source 18 contacts the upstream portion 52 of the first resilient member 48 and the volatile delivery enhancing compound source 22 contacts the downstream portion 54 of the second resilient member 50.

Figure 5:
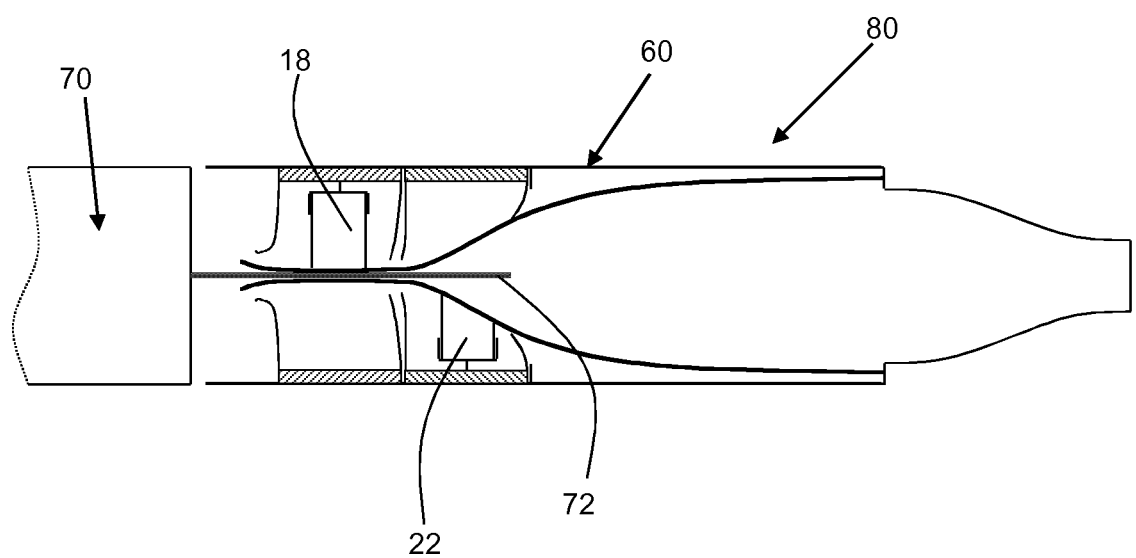
FIG. 5 shows an aerosol-generating device combined with the aerosol-generating article of FIG. 4 to form an aerosol-generating system in accordance with the first embodiment of the present invention.

FIG. 5 shows an aerosol-generating device 70 combined with the aerosol-generating article 60 to form the aerosol-generating system 80 according to the first embodiment of the invention. The aerosol-generating device 70 comprises heater element 72 in the form of a heater blade received between the upstream portions 52 of the resilient members 48 and 50, which are resiliently biased against the heater element 72. The heater element 72 is electrically heated and the aerosol-generating device may comprise a power source and control electronics, as is known in the art. During operation of the aerosol-generating system 80, the heater element 72 heats the medicament source 18 and the volatile delivery enhancing compound source 22. The medicament source 18 contacts the upstream portion 52 of the first resilient member 48, which directly contacts the heater element 72, whereas the volatile delivery enhancing compound source 22 contacts the downstream portion 54 of the second resilient member 50, which is spaced apart from the heater element 72. Therefore, the heater element 72 heats the medicament source 18 to a higher temperature than the volatile delivery enhancing compound source 22.

FIG. 6 shows a first consumable portion 10 of an aerosol-generating article according to a second embodiment of the present invention. The first consumable portion 10 is identical to the first consumable portion described above with respect to FIG. 1 and comprises a tubular segment 12 sealed at both ends by frangible barriers 14 and 16, and the medicament source 18 mounted on an inner surface of the tubular segment 12.

FIG. 7 shows a second consumable portion 100 of the aerosol-generating article according to the second embodiment of the invention. The second consumable portion comprises a housing 102 and a curved passage 104 formed inside the housing 102. The housing 102 is formed from a thermally insulating material, such as a plastic, and may be formed using a molding process to facilitate formation of the curved passage 104.

The housing 102 comprises a recess 106 for receiving the first consumable portion at an upstream end of the housing 102, and a mouthpiece 44 at the downstream end of the housing 102. As described previously, the mouthpiece may be formed integrally with the housing 102 or formed separately and attached to the housing 102. Optionally, the second consumable portion 100 may include a filter 108 at the downstream end of the housing 102, upstream of the mouthpiece 44. The filter may be formed from any suitable filter material known in the art, such as cellulose acetate.

A resilient member 110 is provided in the curved passage 104 and comprises a downstream end secured at the downstream end of the curved passage 104. As described previously, the resilient member 110 is formed from a thermally conductive resilient material, such as metal, capable of withstanding the operating temperature of the heater element that contacts the resilient member 110 during operation of the system.

A volatile delivery enhancing compound source 22, as described previously with respect to FIG. 1, is provided on the resilient member 110. A frangible barrier 112 seals the upstream end of the curved passageway 104. Preferably, a removable cover covers and seals the mouthpiece 44 to seal the downstream end of the second consumable portion 100.

FIG. 8 shows the first consumable portion 10 inserted into the recess 106 of the second consumable portion 100 so that the first and second consumable portions 10 and 100 together form the aerosol-generating article 120 according to the second embodiment of the invention. The first consumable portion 10 is retained within the recess 106 by an interference fit between the tubular segment 12 and the housing 102.

FIG. 9 shows the aerosol-generating article 120 combined with the aerosol-generating device 70, described above, to form the aerosol-generating system 130 in accordance with the second embodiment of the present invention. Upon combining the aerosol-generating article 120 with the aerosol-generating device 70, the heater element 72 is inserted into the first consumable portion 10 and the upstream end of the curved passage 104. Insertion of the heater element 72 into the aerosol-generating article 120 ruptures the frangible barriers 14, 16 and 112 and allows air to flow into the upstream end of the aerosol-generating article 120, through the first consumable portion 10, the curved passage 104 and out of the downstream end of the aerosol-generating article 120 through the mouthpiece 44.

The downstream end of the heater element 72 contacts the upstream end of the resilient member 110 so that the resilient member 110 is resiliently biased against the heater element 72. During operation of the aerosol-generating system 130, the heater element 72 heats the medicament source 18 and the volatile delivery enhancing compound source 22. The medicament source 18 directly contacts the heater element 72, whereas the volatile delivery enhancing compound source 22 is heated via the resilient member 110. Therefore, the heater element 72 heats the medicament source 18 to a higher temperature than the volatile delivery enhancing compound source 22.

Figure 10:
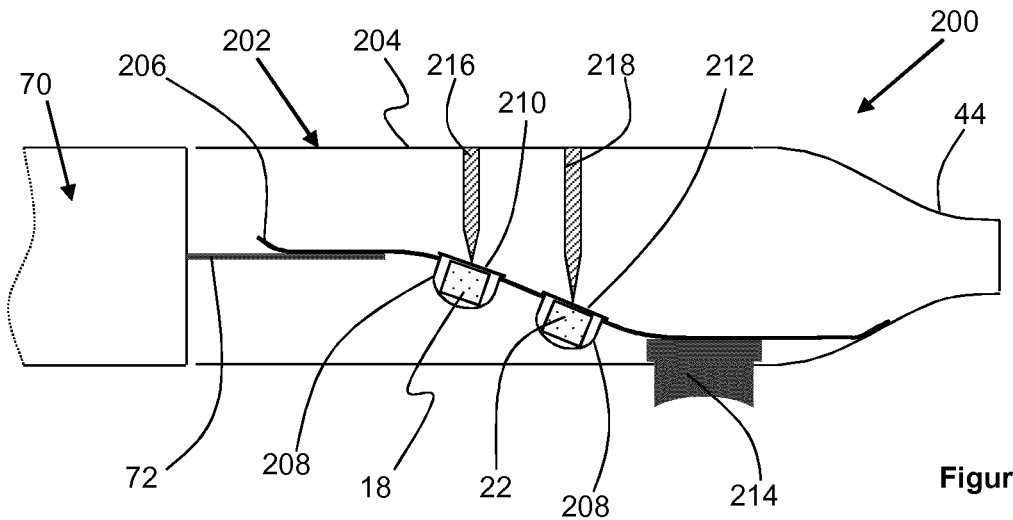
FIG. 10 shows an aerosol-generating system in accordance with a third embodiment of the present invention.

FIG. 10 shows an aerosol-generating system 200 in accordance with a third embodiment of the present invention. The aerosol-generating system comprises an aerosol-generating article 202 in combination with an aerosol-generating device 70, as described with respect to the previous embodiments.

The aerosol-generating article 202 comprises an outer housing 204 and a mouthpiece 44. As described previously, the mouthpiece 44 may be formed integrally with the outer housing 204, or the mouthpiece 44 may be formed separately. The outer housing 204 and the mouthpiece 44 are formed from a thermally insulating material, such as a plastic.

A medicament source 18 and a volatile delivery enhancing source 22, both as described previously, are provided on a resilient member 206. In the embodiment shown in FIG. 10, each of the medicament source 18 and the volatile delivery enhancing compound source 22 is provided in a recess 208 in the resilient member 206. However, the two sources could alternatively be provided on the surface of the resilient member 206. Frangible barriers 210 and 212 formed from a metal foil seal the medicament source 18 and the volatile delivery enhancing compound source 22 respectively. As described previously, the resilient member 206 is formed from a thermally conductive resilient material, such as metal, capable of withstanding the operating temperature of the heater element that contacts the resilient member 206 during operation of the system. With the heater element 72 of the aerosol-generating device 70 inserted into the aerosol-generating article 202, the heater element 72 contacts the upstream end of the resilient member 206 so that the resilient member 206 is resiliently biased against the heater element 72.

A downstream end of the resilient member 206 is secured to the outer housing 204 and a push-button 214 is attached to the resilient member 206. The push-button 214 extends through an aperture in the outer housing 204 so that the push-button 214 is accessible to a user. First and second piercing elements 216 and 218 extend from an inner surface of the outer housing 204 and overlie the medicament source 18 and the volatile delivery enhancing compound source 22 respectively. To activate the aerosol-generating article, a user pushes on the push-button 214 to deflect the resilient member 206 towards the first and second piercing elements 216 and 218 so that the first and second piercing element 216 and 218 pierce the frangible barriers 210 and 212. After releasing the push-button 204 the resilient member 206 returns to the pre-activation position so that the upstream end of the resilient member 206 is resiliently biased against the heater element 72.

During operation of the aerosol-generating system 200, the heater element 72 heats the medicament source 18 and the volatile delivery enhancing compound source 22 via the resilient member 206. The medicament source 18 is positioned on the resilient member 206 upstream from the volatile delivery enhancing compound source 22 and therefore closer to the heater element 72. Accordingly, the heater element 72 heats the medicament source 18 to a higher temperature than the volatile delivery enhancing compound source 22.

Figure 11:
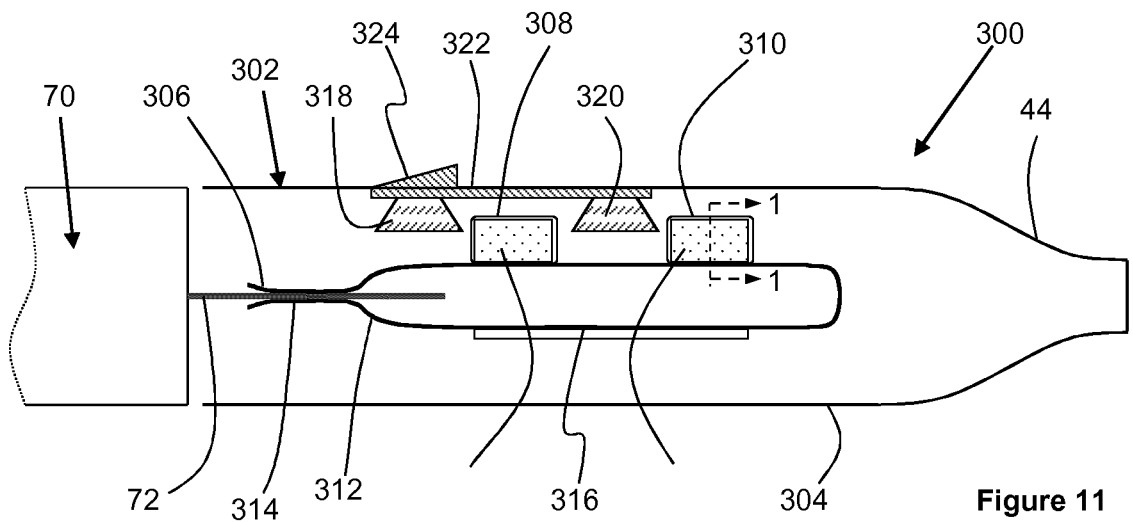
FIG. 11 shows an aerosol-generating system in accordance with a fourth embodiment of the present invention.

FIG. 11 shows an aerosol-generating system 300 in accordance with a fourth embodiment of the present invention. The aerosol-generating system 300 comprises an aerosol-generating article 302 in combination with an aerosol-generating device 70, as described with respect to the previous embodiments.

The aerosol-generating article 302 comprises an outer housing 304 and a mouthpiece 44. As described previously, the mouthpiece 44 may be formed integrally with the outer housing 304, or the mouthpiece 44 may be formed separately. The outer housing 304 and the mouthpiece 44 are formed from a thermally insulating material, such as a plastic.

A medicament source 18 and a volatile delivery enhancing compound source 22, both as described previously, are provided on a first resilient member 306. Frangible barriers 308 and 310 formed from a metal foil seal the medicament source 18 and the volatile delivery enhancing compound source 22 respectively. A second resilient member 312 is also provided within the outer housing 304, the first and second resilient members 306 and 312 each having an upstream portion 314 and a downstream portion 316. The upstream portions 314 of the first and second resilient members 306 and 312 are positioned adjacent each other and arranged to grip the heater element 72 of the aerosol-generating device 70 when inserted into the aerosol-generating article 302. The downstream portions 316 of the first and second resilient members 306 and 312 are spaced apart.

In the embodiment shown in FIG. 11, the first and second resilient members 306 and 312 are formed from a single piece of resilient material so that the downstream portions 316 of the resilient member are connected at their downstream ends by a continuous portion of the resilient material. However, the first and second resilient members 306 and 312 can alternatively be formed separately and separately mounted within the outer housing 304.

As described previously, the resilient members 306 and 312 are formed from a thermally conductive resilient material, such as metal, capable of withstanding the operating temperature of the heater element that contacts the upstream portions 314 of the resilient members 306 and 312 during operation of the system. With the heater element 72 of the aerosol-generating device 70 inserted into the aerosol-generating article 302, the heater element 72 contacts the upstream portions 314 of the resilient members 306 and 312 so that the upstream portions 314 are resiliently biased against the heater element 72.

The aerosol-generating device 302 also comprises first and second cutting blades 318 and 320 mounted on a carrier element 322. The carrier element 322 is slidably mounted on the outer housing 304 and comprises a push-button 324 that extends through an elongate slot in the outer housing 304. To activate the aerosol-generating article 302, a user pushes on the push-button 324 to slide the carrier element 322 along the outer housing 304, so that the first and second cutting blades 318 rupture the frangible barriers 308 and 310. The aerosol-generating device 302 may further comprise a resilient biasing element, such as a spring, to return the carrier element 322 to the pre-activation position when the user releases the push-button 324.

During operation of the aerosol-generating system 300, the heater element 72 heats the medicament source 18 and the volatile delivery enhancing compound source 22 via the first resilient member 306. The medicament source 18 is positioned on the first resilient member 306 upstream from the volatile delivery enhancing compound source 22 and therefore closer to the heater element 72. Accordingly, the heater element 72 heats the medicament source 18 to a higher temperature than the volatile delivery enhancing compound source 22.

Figure 12:
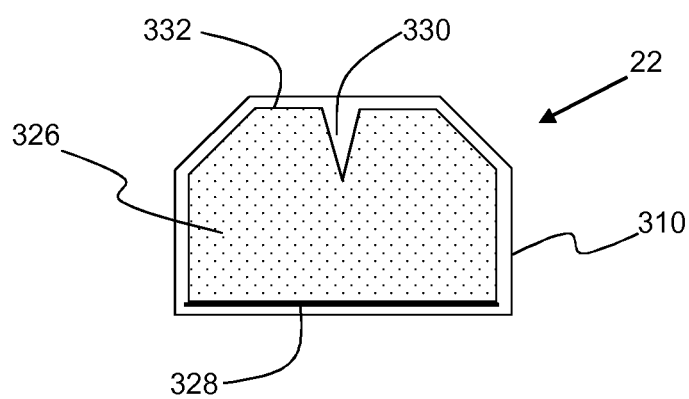
FIG. 12 shows a cross-sectional view of the volatile delivery enhancing compound source of the aerosol-generating system of FIG. 11.

FIG. 12 shows a transverse cross-sectional view of the volatile delivery enhancing compound source 22 taken along line 1-1 in FIG. 11. The volatile delivery enhancing compound source comprises a sorption element 326 onto which the volatile delivery enhancing compound is sorbed. In this embodiment, the sorption element 326 is mounted on a base plate 328 and the entire volatile delivery enhancing compound source is wrapped in the frangible barrier 310. A V-shaped slot 330 is provided in the upper surface 332 of the sorption element 326 and extends along the entire length of the upper surface 332. During activation of the aerosol-generating article 302, the second cutting blade 318 passes along the V-shaped slot 330 to rupture the frangible barrier 310. In this embodiment, the medicament source 18 is constructed in an identical manner to the volatile delivery enhancing compound source 22 and therefore also comprises a V-shaped slot in the upper surface of a sorption element.

Figure 13:
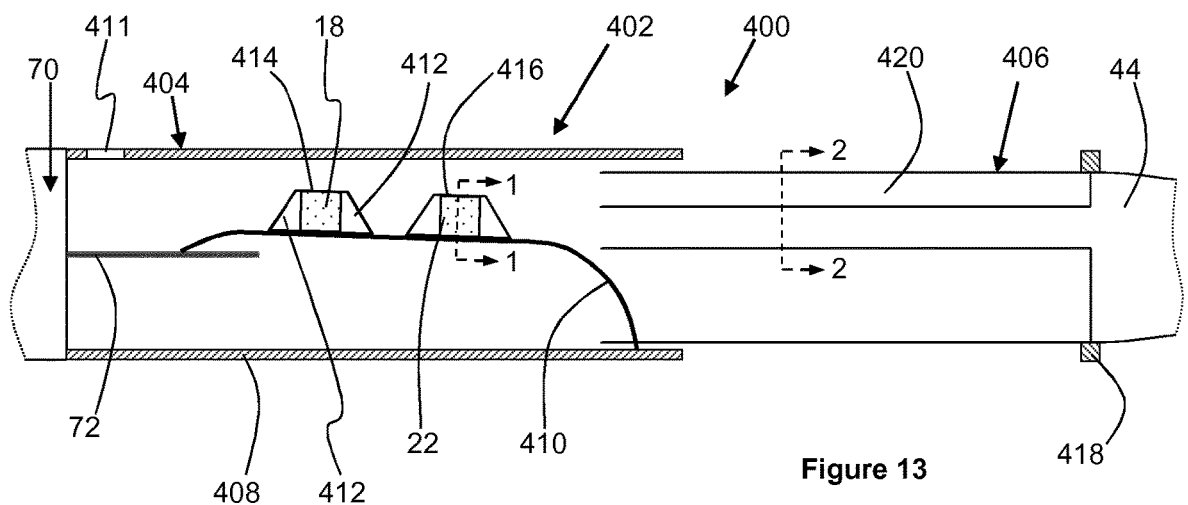
FIG. 13 shows an aerosol-generating system in accordance with a fifth embodiment of the present invention, before activation of the aerosol-generating article.

FIG. 13 shows an aerosol-generating system 400 in accordance with a fifth embodiment of the present invention. The aerosol-generating system 400 comprises an aerosol-generating article 402 in combination with an aerosol-generating device 70, as described with respect to the previous embodiments.

The aerosol-generating article 402 comprises a housing portion 404 connected to the aerosol-generating device 70 and an insert portion 406 slidably received within a downstream end of the housing portion 404.

The housing portion 404 comprises an outer housing 408, a resilient member 410 connected at its downstream end to the outer housing 408, and an airflow inlet 411 in an upstream end of the outer housing 408. A medicament source 18 and a volatile delivery enhancing compound source 22, both as described previously, are provided on the resilient member 410. Rigid supports 412 are provided adjacent each end of each of the medicament source 18 and the volatile delivery enhancing compound source 22. Frangible barriers 414 and 416 formed from a metal foil seal the medicament source 18 and the volatile delivery enhancing compound source 22 respectively. For ease of constructing the aerosol-generating article 402, preferably the frangible barriers also wrap around the rigid supports 412, as described in more detail below with reference to FIG. 15.

An upstream end of the resilient member 410 is resiliently biased against the heater element 72 of the aerosol-generating device 70. As described with respect to previous embodiments, the resilient member 410 is formed from a thermally conductive resilient material, such as metal, capable of withstanding the operating temperature of the heater element 72.

The insert portion 406 comprises an annular stopper 418 and a mouthpiece 44, as described previously, extending downstream from the annular stopper 418. Extending upstream from the annular stopper 418 and the mouthpiece 44 is a rupturing portion 420, which is described in more detail below with respect to FIG. 16.

Figure 15:
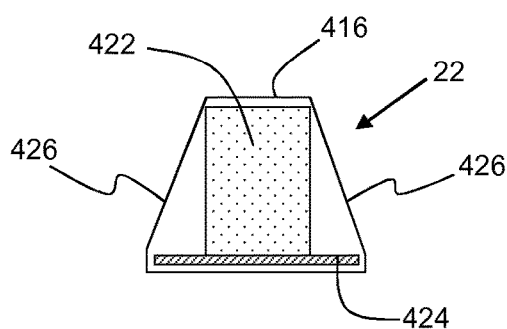
FIG. 15 shows a cross-sectional view of the volatile delivery enhancing compound source of the aerosol-generating system of FIGS. 13 and 14.

FIG. 15 shows a transverse cross-sectional view of the volatile delivery enhancing compound source 22 taken along line 1-1 in FIG. 13. The volatile delivery enhancing compound source comprises a sorption element 422 onto which the volatile delivery enhancing compound is sorbed. The sorption element 422 and the rigid supports 412 at each end of the sorption element 422 are mounted on a base plate 424 and the base plate 424, the rigid supports 412 and the sorption element 422 are wrapped in the frangible barrier 416. The transverse cross-sectional shape of the rigid supports 412 is the same as the transverse cross-sectional shape of the sorption element 422, and the width of the base plate 424 is larger than the width of the sorption element 422 and the rigid supports 412. Therefore, the side portions 426 of the frangible barrier 416 are spaced apart from the sorption element 422 and the rigid supports 412. In this embodiment, the medicament source 18 is constructed in an identical manner to the volatile delivery enhancing compound source 22.

Figure 14:
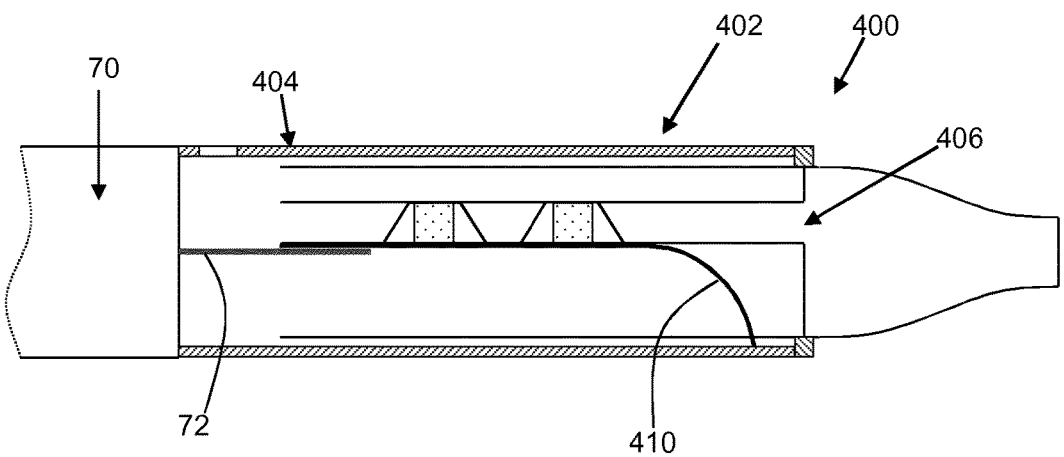
FIG. 14 shows the aerosol-generating system of FIG. 13 after activation of the aerosol-generating article.
Figure 16:
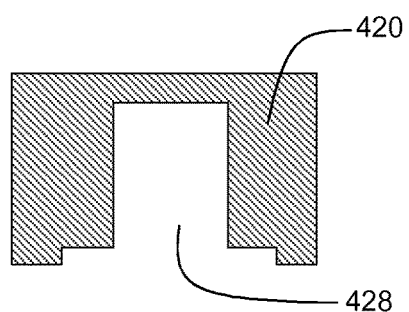
FIG. 16 shows a cross-sectional view of a moveable part of the aerosol-generating system of FIGS. 13 and 14.

FIG. 16 shows a transverse cross-sectional view of the rupturing portion 420 taken along line 2-2 in FIG. 13. As shown by comparing FIGS. 15 and 16, the rupturing portion 420 comprises a longitudinal cut-out 428 having a transverse cross-sectional shape that is slightly larger than the combined transverse cross-sectional shape of the sorption element 422 and the base plate 424. Therefore, to activate the aerosol-generating article 402, a user pushes the insertion portion 406 into the housing portion 404 until the annular stopper 418 abuts the downstream end of the outer housing 408. As the insertion portion 406 slides into the housing portion 404, the rupturing portion 420 pushes against the side portions 426 of the frangible barriers 414 and 416 and therefore ruptures the frangible barriers 414 and 416. At the same time, the rupturing portion 420 further depresses the resilient member 410 against the heater element 72 to ensure optimum contact between the resilient member 410 and the heater element 72, as shown in FIG. 14.

During operation of the aerosol-generating system 400, the heater element 72 heats the medicament source 18 and the volatile delivery enhancing compound source 22 via the resilient member 410. The medicament source 18 is positioned on the resilient member 410 upstream from the volatile delivery enhancing compound source 22 and therefore closer to the heater element 72. Accordingly, the heater element 72 heats the medicament source 18 to a higher temperature than the volatile delivery enhancing compound source 22.

Figure 17:
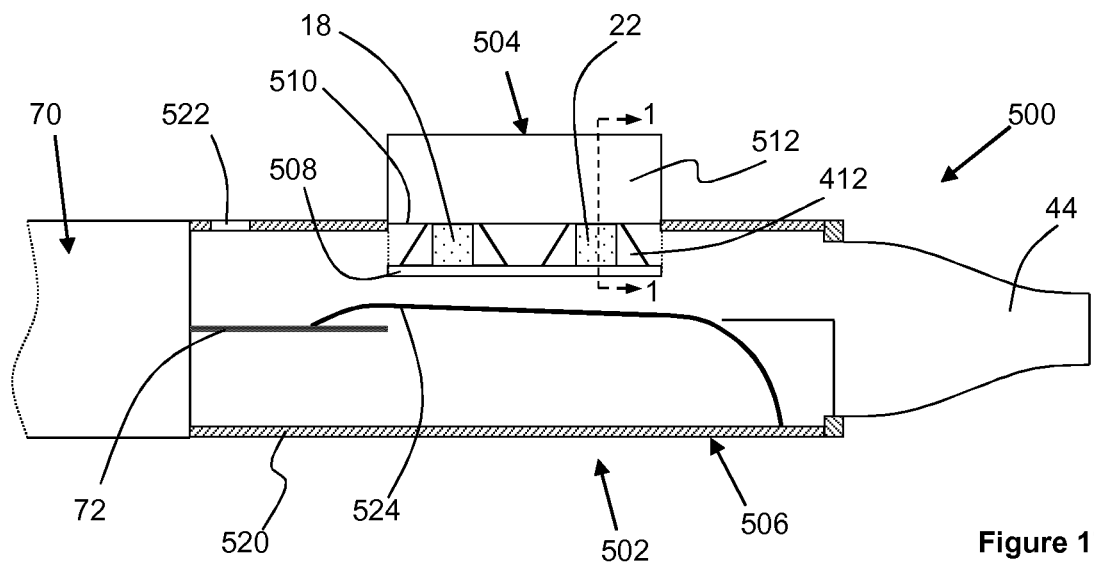
FIG. 17 shows an aerosol-generating system in accordance with a sixth embodiment of the present invention, before activation of the aerosol-generating article.

FIG. 17 shows an aerosol-generating system 500 in accordance with a sixth embodiment of the present invention. The aerosol-generating system 500 comprises an aerosol-generating article 502 in combination with an aerosol-generating device 70, as described with respect to the previous embodiments.

The aerosol-generating article 502 comprises a consumable portion 504 and a reusable portion 506 that attaches to the aerosol-generating device 70. The consumable portion 504 comprises a medicament source 18 and a volatile delivery enhancing compound source 22, both as described previously. Rigid supports 412 are provided adjacent each end of each of the medicament source 18 and the volatile delivery enhancing compound source 22. The medicament source 18, the volatile delivery enhancing compound source 22 and the rigid supports 412 are mounted on a common base plate 508. A frangible barrier 510 formed from a metal foil wraps entirely around the medicament source 18, the volatile delivery enhancing compound source 22, the rigid support 412 and the common base plate 508 to seal the medicament source 18 and the volatile delivery enhancing compound source 22.

Figure 19:
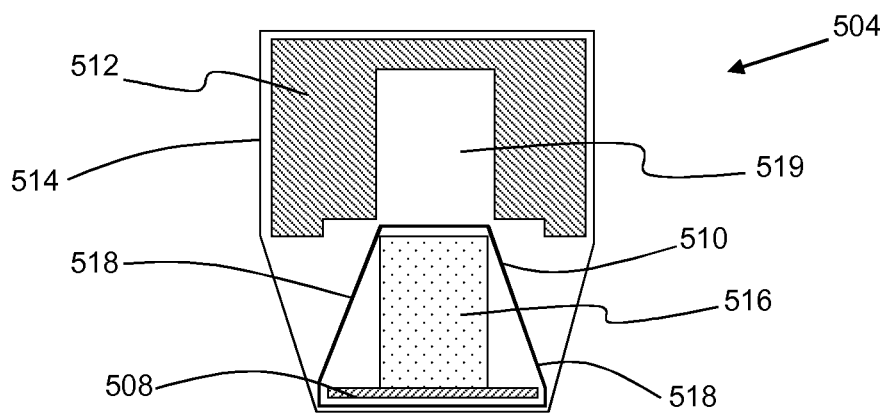
FIG. 19 shows a cross-sectional view of a consumable portion of the aerosol-generating system of FIGS. 17 and 18.

As shown more clearly in FIG. 19, which shows a transverse cross section of the consumable portion 504 taken along line 1-1 in FIG. 17, the consumable portion 504 also comprises a rupturing portion 512 positioned adjacent the medicament source 18, the volatile delivery enhancing compound source 22 and the rigid supports 412. The rupturing portion 512 is connected to the remainder of the consumable portion 504 by a foil wrap 514 that wraps around the top and sides of the rupturing portion 512 and around the bottom of the common base plate 508. The foil wrap 514 does not extend across the upstream and downstream ends of the consumable portion 504 so that an airflow passage is established through the consumable portion 504.

As shown in FIG. 19, the volatile delivery enhancing compound source 22 comprises a sorption element 516 onto which the volatile delivery enhancing compound is sorbed. In this embodiment, the medicament source 18 comprises a similar sorption element having the same transverse cross-sectional shape as the sorption element 516. The transverse cross-sectional shape of the rigid supports 412 is also the same as the transverse cross-sectional shape of the sorption element 516, and the width of the common base plate 508 is larger than the width of the sorption elements and the rigid supports 412. Therefore, the side portions 518 of the frangible barrier 510 are spaced apart from the sorption elements and the rigid supports 412.

As shown in FIG. 19, the rupturing portion 512 comprises a longitudinal cut-out 519 having a transverse cross-sectional shape that is slightly larger than the combined transverse cross-sectional shape of the sorption elements and the common base plate 508. Therefore, to activate the consumable portion 504, a user pushes the rupturing portion 512 towards the medicament source 18 and the volatile delivery enhancing compound source 22 so that the rupturing portion 512 pushes against the side portions 518 of the frangible barrier 510 and ruptures the frangible barrier 510. To prevent accidental activation of the consumable portion 504, the consumable portion 504 may comprise one or more resilient biasing elements, such as one or more springs, positioned between the rupturing portion 512 and the common base plate 508 to bias the rupturing portion 512 away from the common base plate 508. Additionally, or alternatively, the consumable portion 504 may comprise one or more elements that function to retain the rupturing portion 512 against the common base plate 508 after the consumable portion 504 has been activated. For example, an interference fit between the rupturing portion 512 and the common base plate 508 may retain the rupturing portion 512 against the common base plate 508 after the consumable portion 504 has been activated.

The reusable portion 506 comprises an outer housing 520 and a mouthpiece 44 at a downstream end of the outer housing 520, as described previously. The mouthpiece 44 may be formed integrally with the outer housing 520, or the mouthpiece 44 may be formed separately and attached to the outer housing 520. An airflow inlet 522 at the upstream end of the outer housing 520 establishes an airflow passage through the outer housing 520 from the airflow inlet 522 to the mouthpiece 44.

A resilient member 524 is secured at its downstream end to an inner surface of the outer housing 520. An upstream end of the resilient member 524 is resiliently biased against the heater element 72 of the aerosol-generating device 70. As described with respect to previous embodiments, the resilient member 524 is formed from a thermally conductive resilient material, such as metal, capable of withstanding the operating temperature of the heater element 72.

Figure 18:
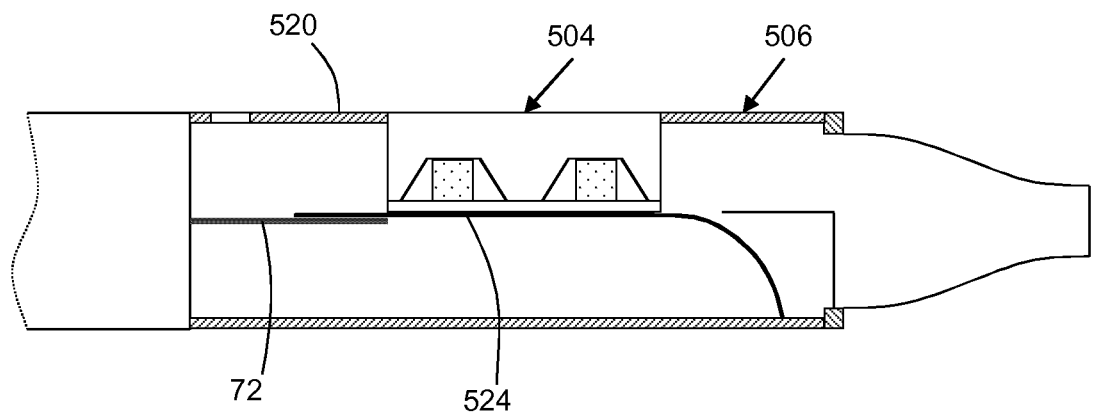
FIG. 18 shows the aerosol-generating system of FIG. 17 after activation of the aerosol-generating article.

To prepare the aerosol-generating system 500 for operation, the consumable portion 504 is inserted into the reusable portion 506 through an aperture in a sidewall of the outer housing 520. Pushing the consumable portion 504 into the reusable portion 506 further depresses the resilient member 524 against the heater element 72 to ensure optimum contact between the resilient member 524 and the heater element 72, as shown in FIG. 18. The consumable portion 504 may be pre-activated by the user, or the action of pushing the consumable portion 504 against the resilient member 524 may activate the consumable portion 504.

During operation of the aerosol-generating system 500, the heater element 72 heats the medicament source 18 and the volatile delivery enhancing compound source 22 via the resilient member 524 and the common base plate 508. For this reason, the common base plate 508 is also constructed from a thermally conductive material, such as a metal. The medicament source 18 is positioned on the common base plate 508 upstream from the volatile delivery enhancing compound source 22 and therefore closer to the heater element 72. Accordingly, the heater element 72 heats the medicament source 18 to a higher temperature than the volatile delivery enhancing compound source 22.

Figure 20:
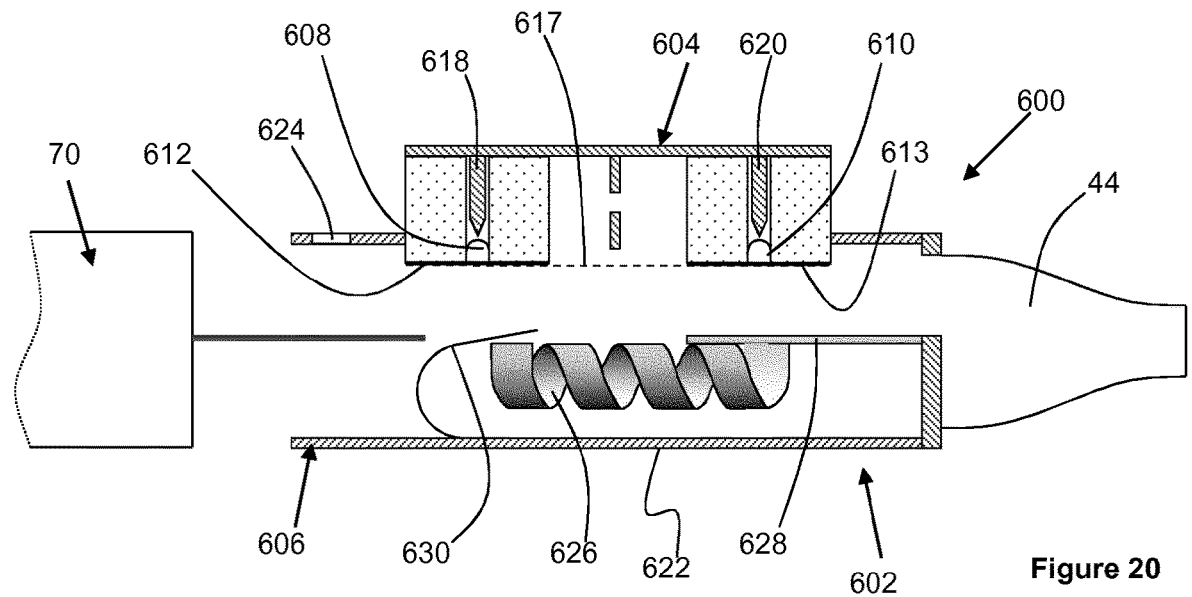
FIG. 20 shows an aerosol-generating system in accordance with a seventh embodiment of the present invention, before activation of the aerosol-generating article and before full insertion of the aerosol-generating device into the aerosol-generating article.
Figure 21:
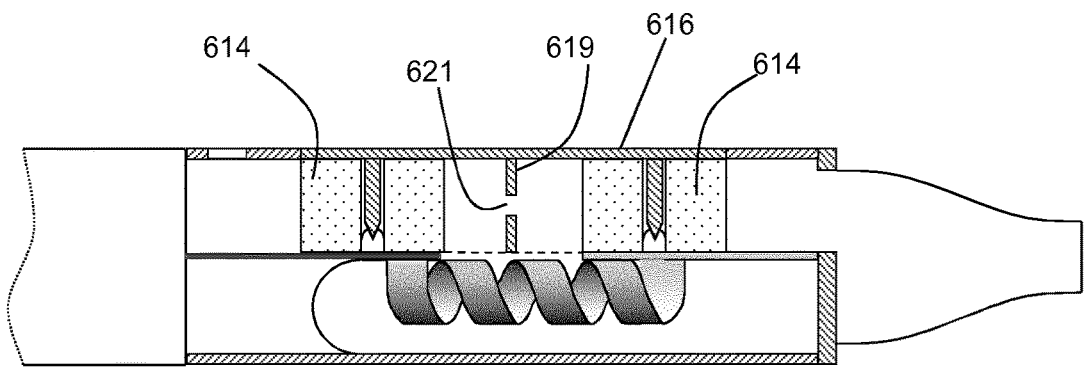
FIG. 21 shows the aerosol-generating system of FIG. 20 after activation of the aerosol-generating article and after full insertion of the aerosol-generating device into the aerosol-generating article.
Figure 22:
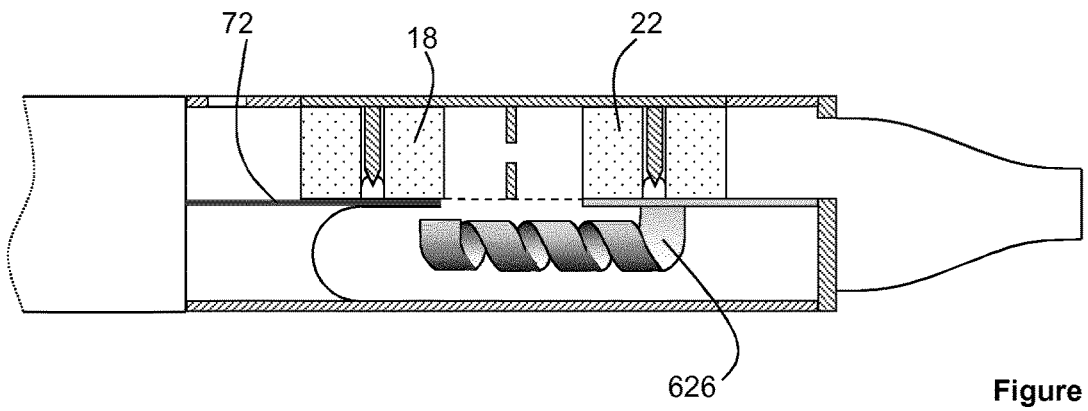
FIG. 22 shows the aerosol-generating system of FIG. 21 after the volatile delivery enhancing compound source has been heated to a predetermined temperature.

FIGS. 20, 21 and 22 show an aerosol-generating system 600 in accordance with a seventh embodiment of the present invention. The aerosol-generating system 600 comprises an aerosol-generating article 602 in combination with an aerosol-generating device 70, as described with respect to the previous embodiments.

The aerosol-generating article 602 comprises a consumable portion 604 and a reusable portion 606 that attaches to the aerosol-generating device 70. The consumable portion 604 comprises a medicament blister 608 and a volatile delivery enhancing compound blister 610. The medicament blister 608 comprises a blister containing a liquid medicament, such as nicotine. The blister forms a frangible barrier sealing the medicament and is formed from a non-permeable material, such as a plastic. Similarly, the volatile delivery enhancing compound blister 610 comprises a blister containing a liquid volatile delivery enhancing compound. The blister forms a frangible barrier sealing the volatile delivery enhancing compound and is formed from a non-permeable material, such as a plastic.

The medicament blister 608 and the volatile delivery enhancing compound blister 610 are each mounted on a base plate 612 and 613 and each contained within a channel in a compressible sorption element 614. A top plate 616 overlies the sorption elements 614 and comprises side walls that extend downwardly and overlap similar side walls extending upwardly from each base plate 612 and 613. A captive mechanism, such as overlapping flanges on the side walls of the top plate 616 and each base plate 612 and 613, prevents the top plate 616 and the base plates 612 and 613 from becoming detached from each other. An overwrap 617 wraps around the top, sides and bottom of the consumable portion 604 to define an airflow passage between the upstream and downstream ends of the consumable portion 604.

First and second piercing elements 618 and 620 extend from an inner surface of the top plate 616 and overlie the medicament blister 608 and the volatile delivery enhancing compound blister 610 respectively. A restriction plate 619 comprising an airflow aperture 621 also extends from the inner surface of the top plate 616. To activate the consumable portion 604, a user depresses the top plate 616 towards the base plates 612 and 613 to compress the sorption elements 614 and to pierce the medicament blister 608 and the volatile delivery enhancing compound blister 610 with the first and second piercing elements 618 and 620. Upon piercing the blisters, the medicament and the volatile delivery enhancing compound are released and are at least partially sorbed onto the sorption elements 614 so that the sorption elements form a medicament source 18 and a volatile delivery enhancing compound source 22.

To prevent accidental activation of the consumable portion 604, the consumable portion 604 may comprise one or more resilient biasing elements, such as one or more springs, positioned between the top plate 616 and the base plates 612 and 613 to bias the top plate 616 away from the base plates 612 and 613. Additionally, or alternatively, the consumable portion 604 may comprise one or more elements that function to retain the top plate 616 and the base plates 612 and 613 in the activated position after the consumable portion 604 has been activated. For example, an interference fit between a portion of the top plate 616 and a portion of each base plate 612 and 613 may retain the top plate 616 and the base plates 612 and 613 in the activated position after the consumable portion 604 has been activated.

The reusable portion 606 comprises an outer housing 622 and a mouthpiece 44 at a downstream end of the outer housing 622, as described previously. The mouthpiece 44 may be formed integrally with the outer housing 622, or the mouthpiece 44 may be formed separately and attached to the outer housing 622. An airflow inlet 624 at the upstream end of the outer housing 622 establishes an airflow passage through the outer housing 622 from the airflow inlet 624 to the mouthpiece 44.

A resilient member 626 comprises a thermally conductive element 628 extending from a downstream end of the housing and a bimetallic strip secured at its downstream end to the thermally conductive element 628. An upstream end of the bimetallic strip is resiliently biased against the heater element 72 of the aerosol-generating device 70 when the heater element 72 is inserted into the reusable portion 606, as shown in FIG. 21. To ensure correct and optimum contact between the heater element 72 and the upstream end of the bimetallic strip, a resilient contact spring 630 may be positioned adjacent the upstream end of the bimetallic strip. Although the bimetallic strip is illustrated as having a spiral shape, other shapes could also be used. For example, a simple flat bimetallic strip can be attached at its downstream end to the thermally conductive element 628 to form a bimetallic cantilever.

To prepare the aerosol-generating system 600 for operation, the consumable portion 604 is inserted into the reusable portion 606 through an aperture in a sidewall of the outer housing 622. Pushing the consumable portion 604 into the reusable portion 606 brings the base plate 612 into contact with the heater element 72 and brings the base plate 613 into contact with the thermally conductive element 628, as shown in FIG. 21. The consumable portion 604 may be pre-activated by the user, or the action of pushing the consumable portion 604 into the reusable portion may activate the consumable portion 604.

During operation of the aerosol-generating system 600, the heater element 72 heats the medicament source 18 via the base plate 612 and heats the volatile delivery enhancing compound source 22 via the resilient member 626 in the form of the bimetallic strip, the thermally conductive element 628 and the base plate 613. For this reason, the base plates 612 and 613 are constructed from a thermally conductive material, such as a metal. The bimetallic strip is configured, through appropriate choice of the metals forming the strip and the shape of the strip, to undergo mechanical displacement of the upstream end of the bimetallic strip away from the heater element 72 when a predetermined temperature is reached, as shown in FIG. 22. Once the predetermined temperature is reached, the upstream end of the bimetallic strip no longer contacts the heater element 72, so that the volatile delivery enhancing compound source 22 is no longer heated. As the bimetallic strip cools again it returns to its pre-heating shape and position so that its upstream end re-contacts the heater element 72. In this way, the bimetallic strip provides thermostatic control of the heating of the volatile delivery enhancing compound source 22. By appropriate selection of the predetermined temperature at which the switching of the bimetallic strip occurs, the heater element 72 heats the medicament source 18 to a higher temperature than the volatile delivery enhancing compound source 22.

Figure 23:
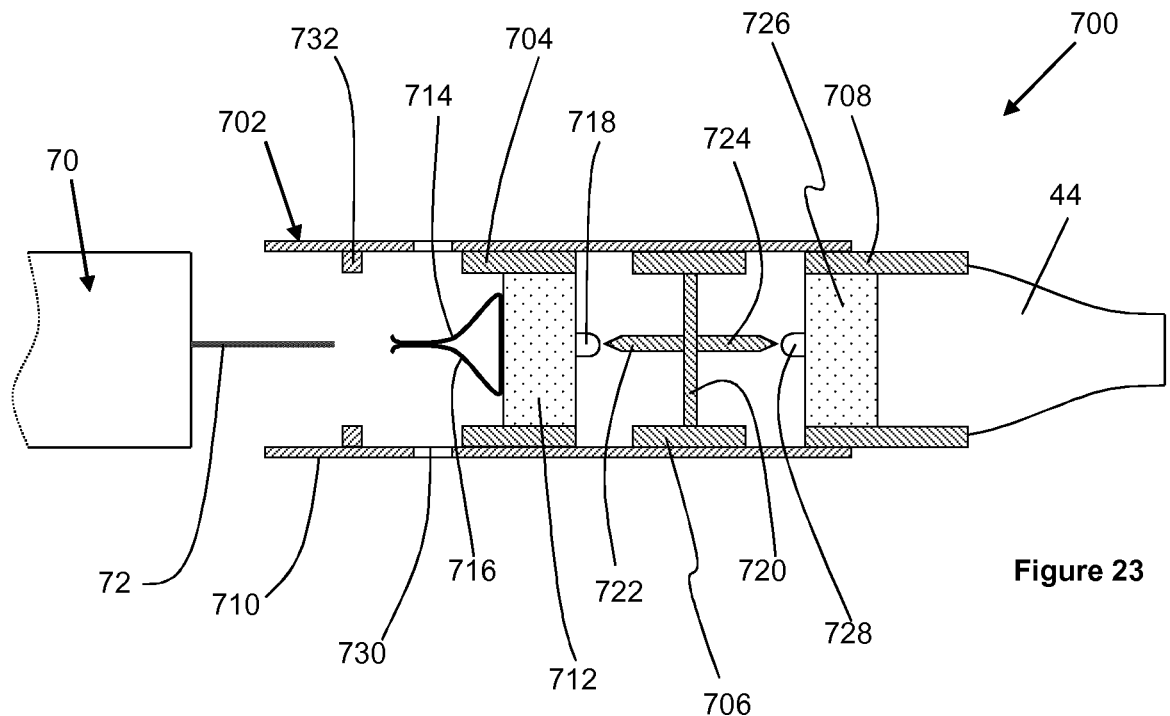
FIG. 23 shows an aerosol-generating system in accordance with an eighth embodiment of the present invention, before activation of the aerosol-generating article and before full insertion of the aerosol-generating device into the aerosol-generating article.
Figure 24:
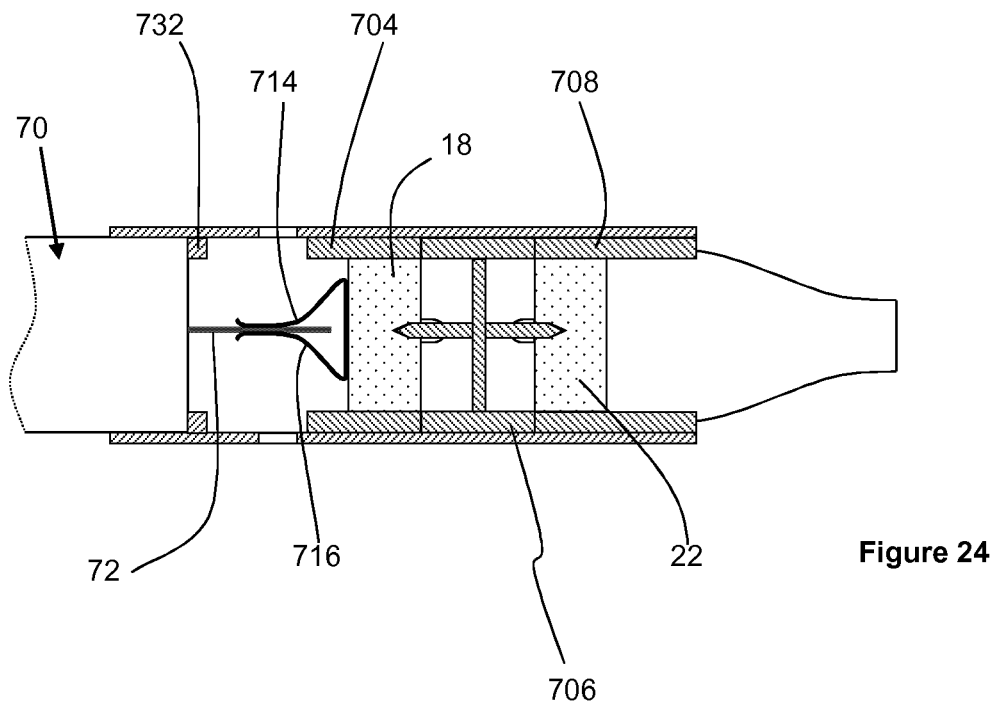
FIG. 24 shows the aerosol-generating system of FIG. 23 after activation of the aerosol-generating article and after full insertion of the aerosol-generating device into the aerosol-generating article.

FIGS. 23 and 24 show an aerosol-generating system 700 according to an eighth embodiment of the present invention. The aerosol-generating system 700 comprises an aerosol-generating article 702 in combination with an aerosol-generating device 70, as described previously.

The aerosol generating article 702 comprising a first tubular segment 704, a second tubular segment 706 and a third tubular segment 708, all received within a tubular outer housing 710. The first tubular segment 704 is fixed within the outer housing 710, and the second and third tubular segments 706 and 708 are slidably received within the outer housing 710.

A first sorption element 712 is mounted within the first tubular segment 704 and comprises an upstream face and a downstream face. First and second resilient members 714 and 716 are provided on the upstream face of the first sorption element 712 and are positioned adjacent each other to receive the heater element 72 of the aerosol-generating device 70 between them. When the heater element 72 is inserted into the aerosol-generating article 702, as shown in FIG. 24, the first and second resilient members 714 and 716 are resiliently biased against the heater element 72 so that they grip the heater element 72.

As described with respect to previous embodiments, the resilient members 714 and 716 are formed from a thermally conductive resilient material, such as metal, capable of withstanding the operating temperature of the heater element. In the embodiment shown in FIG. 23, the first and second resilient members 714 and 716 are formed from a single piece of resilient material so that the downstream ends of the resilient members are connected by a continuous portion of the resilient material. However, the first and second resilient members 714 and 716 can alternatively be formed separately and separately mounted on the first sorption element 712.

Depending on the material used to form the first sorption element 712, it may be preferable to provide an intermediate mounting plate formed from a rigid thermally conductive material between the first sorption element 712 and the resilient members 714 and 716.

A medicament blister 718 is provided on the downstream face of the first sorption element 712. The medicament blister comprises a liquid medicament contained within a blister, as described previously with respect to the embodiment shown in FIG. 20. The blister forms a frangible barrier containing the liquid medicament.

The second tubular segment 706 comprises a divider plate 720 mounted within the second tubular segment 706. A first piercing element 722 extends from the upstream face of the divider plate 720 and a second piercing element 724 extends from the downstream face of the divider plate 720.

The third tubular segment 708 comprises a second sorption element 726 mounted within the first tubular segment 704 and comprising an upstream face and a downstream face. A volatile delivery enhancing compound blister 728 is provided on the upstream face of the second sorption element 726 and comprises a liquid volatile delivery enhancing compound contained within a blister, as described previously with respect to the embodiment shown in FIG. 20. The blister forms a frangible barrier containing the liquid volatile delivery enhancing compound. A mouthpiece 44, as described previously, extends downstream from the third tubular segment 708.

The aerosol-generating device 702 also comprises airflow inlets 730 in the outer housing 710 upstream of the first tubular segment 704, and an annular stopper 732 provided on an inner surface of the outer housing 710 upstream of the first and second resilient members 714 and 716. The aerosol-generating device 70 is inserted into the aerosol-generating article 702 until the aerosol-generating device 70 abuts the annular stopper 732, as shown in FIG. 23.

To activate the aerosol-generating article 702, a user pushes the third tubular segment 708 into the outer housing 710 so that the third tubular segment 708 pushes the second tubular segment 706 towards the first tubular segment 704. The user continues to push the third tubular segment 708 until the second tubular segment 706 abuts the first tubular segment 704 and the third tubular segment 708 abuts the second tubular segment 706, as shown in FIG. 24. Pushing the three tubular segments together causes the first and second piercing elements 722 and 724 to pierce the medicament blister 718 and the volatile delivery enhancing compound blister 728, which releases the liquid medicament and the liquid volatile delivery enhancing compound onto the respective sorption elements. The first sorption element 712 with at least some of the medicament sorbed thereon forms a medicament source 18 that contacts the first and second resilient members 714 and 716. Similarly, the second sorption element 726 with at least some of the volatile delivery enhancing compound sorbed thereon forms a volatile delivery enhancing compound source 22.

During operation of the aerosol-generating system 700, the heater element 72 heats the medicament source 18 via the first and second resilient members 714 and 716. The volatile delivery enhancing compound source 22, which is positioned further downstream, is heated via the first and second resilient members 714 and 716, and the first, second and third tubular segments 704, 706 and 708. Therefore, the heater element 72 heats the medicament source 18 to a higher temperature than the volatile delivery enhancing compound source 22.

FIGS. 25 and 26 show an aerosol-generating system 800 in accordance with a ninth embodiment of the present invention. The aerosol-generating system 800 comprises an aerosol-generating article 802 and an aerosol-generating device 70, as described previously.

The aerosol-generating article 802 comprises a tubular outer housing 804 in which an upstream annular stopper 806 and a downstream annular stopper 808 are mounted. Extending between the annular stoppers 806 and 808 are a first rupturing member 810 and a second rupturing member 812 each comprising an elongate plate having an upstream protrusion 814 and a downstream protrusion 816. The protrusions 814 and 816 on the first rupturing member 810 each comprise one or more airflow apertures 818 to allow airflow to enter the space between the first and second rupturing members 810 and 812. An airflow inlet 819 in the outer housing 804 allows air to flow into the aerosol-generating article 802.

A push-button 820 shaped for insertion into the recess forming the downstream protrusion 816 on the first rupturing member 810 extends through an aperture in the outer housing 804. The push-button 820 allows a user to selectively block and unblock the airflow apertures 818 in the upstream protrusion of the first rupturing member 810 to prevent or allow the flow of air through the aerosol-generating article 802 after the aerosol-generating article 802 has been activated. The push-button 820 is shown in the blocked position in FIG. 25 and the unblocked position in FIG. 26.

The aerosol-generating article 802 further comprises a tubular segment 822 slidably received within the downstream end of the outer housing 804. A mouthpiece 44, as described previously, extends downstream from the tubular segment 822. A resilient member 824 extends upstream from the tubular segment 822 and is positioned between the first and second rupturing members 810 and 812. The resilient member 824 is resiliently biased against the heater element 72 of the aerosol-generating device 70. As described with respect to previous embodiments, the resilient member 824 is formed from a thermally conductive resilient material, such as a metal, capable of withstanding the operating temperature of the heater element 72.

A medicament blister 826 is provided on the resilient member 824, the medicament blister 826 comprising a blister containing a liquid medicament, as described with respect to previous embodiments. The blister forms a frangible barrier containing the liquid medicament. Similarly, a volatile delivery enhancing compound blister 828 is provided on the resilient member 824, the volatile delivery enhancing compound blister 828 comprising a blister containing a liquid volatile delivery enhancing compound, as described with respect to previous embodiments. The blister forms a frangible barrier containing the liquid volatile delivery enhancing compound. First and second sorption elements 830 and 832 are provided on the resilient member 824 adjacent the medicament and volatile delivery enhancing compound blisters 826 and 828 respectively.

To activate the aerosol-generating article 802, a user slides the tubular segment 822 into the outer housing 804 until the tubular segment abuts the downstream annular stopper 808. Sliding the tubular segment 822 into the outer housing 804 also slides the resilient member 824 further into the housing outer 804 so that the medicament and volatile delivery enhancing compound blisters 826 and 828 are crushed and ruptured between the upstream and downstream protrusions 814 and 816 of the first and second rupturing members 810 and 812, as shown in FIG. 26. Rupturing the blisters causes at least some of the medicament and the volatile delivery enhancing compound source to be sorbed onto the first and second sorption elements 830 and 832 respectively. The first sorption element 830 with at least some of the medicament sorbed thereon forms a medicament source 18 that contacts the resilient member 824. Similarly, the second sorption element 832 with at least some of the volatile delivery enhancing compound sorbed thereon forms a volatile delivery enhancing compound source 22 that contacts the resilient member 824 downstream from the medicament source 18.

During operation of the aerosol-generating system 800, the heater element 72 heats the medicament source 18 and the volatile delivery enhancing compound source 22 via the resilient member 824. The medicament source 18 is positioned on the resilient member 824 upstream from the volatile delivery enhancing compound source 22 and therefore closer to the heater element 72. Accordingly, the heater element 72 heats the medicament source 18 to a higher temperature than the volatile delivery enhancing compound source 22.

The invention claimed is:

1. An aerosol-generating system, comprising:
   an aerosol-generating device comprising a heater element;
   an aerosol-generating article comprising:
      a medicament source; and
      a volatile delivery enhancing compound source; and
   at least one resilient member provided in the aerosol-generating device or the aerosol-generating article and being resiliently biased against the heater element,
   wherein at least one of the medicament source and the volatile delivery enhancing compound source contacts the at least one resilient member, and
   wherein the aerosol-generating system is configured to heat the medicament source and the volatile delivery enhancing compound source of the aerosol-generating article so that the medicament source has a higher temperature than that of the volatile delivery enhancing compound source.

2. The aerosol-generating system according to claim 1, wherein the heater element is an elongate heater element comprising a proximal end attached to the aerosol-generating device and a free distal end inserted into the aerosol-generating article, and
   wherein a distance between the proximal end of the heater element and the medicament source is less than a distance between the proximal end of the heater element and the volatile delivery enhancing compound source.

3. The aerosol-generating system according to claim 1, wherein the at least one resilient member comprises first and second resilient members each being resiliently biased against the heater element so that the heater element is positioned between the first and second resilient members.

4. The aerosol-generating system according to claim 3, wherein each of the first and second resilient members comprises a first portion being resiliently biased against the heater element and a second portion being spaced apart from the heater element, and
   wherein the volatile delivery enhancing compound source contacts the second portion of one of the first and second resilient members.

5. The aerosol-generating system according to claim 4, wherein the medicament source contacts the first portion of one of the first and second resilient members.

6. The aerosol-generating system according to claim 1, wherein the aerosol-generating article further comprises a housing containing the medicament source, the volatile delivery enhancing compound source, and the at least one resilient member,
   wherein the medicament source contacts the at least one resilient member, and
   wherein the volatile delivery enhancing compound source and the at least one resilient member contact the housing so that heat is conducted from the heater element to the volatile delivery enhancing compound through the at least one resilient member and the housing.

7. The aerosol-generating system according to claim 6, wherein the housing comprises a heat conductive element forming at least part of an inner surface of the housing, and
   wherein the at least one resilient member and the volatile delivery enhancing compound source contact the heat conductive element.

8. The aerosol-generating system according to claim 1, wherein the medicament source contacts the heater element, and
   wherein the volatile delivery enhancing compound source contacts the at least one resilient member.

9. The aerosol-generating system according to claim 1, wherein the at least one resilient member comprises a single resilient member, and wherein the medicament source and the volatile delivery enhancing compound source contact the single resilient member.

11. The aerosol-generating system according to claim 9, wherein the heater element contacts a portion of the single resilient member upstream of the medicament source or adjacent the medicament source, and wherein the volatile delivery enhancing compound source contacts the single resilient member downstream of the medicament source.

11. The aerosol-generating system according to claim 1, wherein the aerosol-generating device and the aerosol-generating article are configured to heat the volatile delivery enhancing compound source to a temperature of between about 30 degrees Celsius and about 100 degrees Celsius.

12. The aerosol-generating system according to claim 1, wherein the aerosol-generating device and the aerosol-generating article are configured to heat the medicament source to a temperature of between about 50 degrees Celsius and about 150 degrees Celsius.

13. The aerosol-generating system according to claim 1, wherein the medicament source comprises a nicotine source.

14. The aerosol-generating system according to claim 1, wherein the volatile delivery enhancing compound source comprises an acid.

\* \* \* \* \*